(12) United States Patent
Caruthers et al.

(10) Patent No.: US 9,689,820 B2
(45) Date of Patent: Jun. 27, 2017

(54) THERMOGRAPHY FOR BATTERY COMPONENT QUALITY ASSURANCE

(71) Applicant: Purdue Research Foundation, West Lafayette, IN (US)

(72) Inventors: James Michael Caruthers, Lafayette, IN (US); Douglas E. Adams, Brentwood, TN (US); Anand David, Woodbury, MN (US); Peter R. O'Regan, West Lafayette, IN (US); Farshid Sadeghi, West Lafayette, IN (US); Nathan Daniel Sharp, West Lafayette, IN (US); Mark David Suchomel, Sugar Grove, IL (US)

(73) Assignee: Purdue Research Foundation, West Lafayette, IN (US)

( * ) Notice: Subject to any disclaimer, the term of this patent is extended or adjusted under 35 U.S.C. 154(b) by 354 days.

(21) Appl. No.: 14/353,713

(22) PCT Filed: Oct. 25, 2012

(86) PCT No.: PCT/US2012/061944
§ 371 (c)(1),
(2) Date: Apr. 23, 2014

(87) PCT Pub. No.: WO2013/063278
PCT Pub. Date: May 2, 2013

(65) Prior Publication Data
US 2014/0294036 A1    Oct. 2, 2014

Related U.S. Application Data

(60) Provisional application No. 61/551,193, filed on Oct. 25, 2011.

(51) Int. Cl.
*G01N 25/72* (2006.01)
*H01M 10/04* (2006.01)
(Continued)

(52) U.S. Cl.
CPC ........ *G01N 25/72* (2013.01); *H01M 10/0413* (2013.01); *H01M 10/0436* (2013.01);
(Continued)

(58) Field of Classification Search
USPC .......................................................... 374/4, 5
See application file for complete search history.

(56) References Cited

U.S. PATENT DOCUMENTS

| 3,814,943 A | 6/1974 | Baker et al. |
| 4,717,592 A | 1/1988 | Nagao et al. |

(Continued)

FOREIGN PATENT DOCUMENTS

| CN | 103443990 A | 12/2013 |
| CN | 103460488 A | 12/2013 |

(Continued)

OTHER PUBLICATIONS

PCT/US2012/061944, KIPO, Search Report and Written Opinion, 19 pgs Feb. 25, 2013.
PCT/US2012/061944, WIPO, IPRP, 17 pgs. May 8, 2014.

*Primary Examiner* — Minh Phan
*Assistant Examiner* — Leon W Rhodes, Jr.
(74) *Attorney, Agent, or Firm* — John V. Daniluck; Bingham Greenebaum Doll LLP

(57) ABSTRACT

Methods and apparatus for the detection of irregularities in a thin film by measurement of transient thermal response.

28 Claims, 29 Drawing Sheets

(51) Int. Cl.
　　*H01M 10/0525*　　　(2010.01)
　　*H01M 10/058*　　　　(2010.01)
　　*H01M 10/34*　　　　　(2006.01)

(52) U.S. Cl.
　　CPC ...... *H01M 10/058* (2013.01); *H01M 10/0525* (2013.01); *H01M 10/345* (2013.01)

(56) References Cited

U.S. PATENT DOCUMENTS

| | | | |
|---|---|---|---|
| 5,711,603 A * | 1/1998 | Ringermacher | G01N 25/72 374/124 |
| 6,013,915 A * | 1/2000 | Watkins | G01N 25/72 250/341.1 |
| 6,235,425 B1 * | 5/2001 | Hanson | H01M 4/04 29/623.3 |
| 6,517,236 B2 * | 2/2003 | Sun | G01N 25/72 250/341.6 |
| 6,712,502 B2 * | 3/2004 | Zalameda | G01J 5/62 374/124 |
| 7,044,634 B2 * | 5/2006 | Sandvoss | G01N 25/72 374/121 |
| 7,643,608 B2 | 1/2010 | Yukisada et al. | |
| 8,449,176 B2 * | 5/2013 | Shepard | G01J 5/08 374/120 |
| 8,603,194 B2 | 12/2013 | Ito et al. | |
| 8,844,795 B2 | 9/2014 | Yano et al. | |
| 9,028,922 B2 | 5/2015 | Yagi et al. | |
| 9,046,352 B2 | 6/2015 | Aramaki et al. | |
| 2007/0031733 A1 | 2/2007 | Kogetsu et al. | |
| 2011/0039017 A1 | 2/2011 | Okazaki et al. | |
| 2011/0085582 A1 * | 4/2011 | Zagar | G01B 21/085 374/9 |
| 2012/0130694 A1 | 5/2012 | Srivastava et al. | |
| 2012/0132697 A1 | 5/2012 | Yano et al. | |
| 2014/0020235 A1 | 1/2014 | Aramaki et al. | |

FOREIGN PATENT DOCUMENTS

| | | |
|---|---|---|
| CN | 103460497 A | 12/2013 |
| CN | 102931438 B | 3/2016 |
| EP | 1843427 B1 | 4/2009 |
| EP | 2696422 A1 | 2/2014 |
| EP | 2696431 A1 | 2/2014 |
| JP | 11044659 A | 2/1999 |
| JP | 1173948 A | 3/1999 |
| JP | 11339813 A | 12/1999 |
| JP | 2000323137 A | 11/2000 |
| JP | 2001305070 A | 10/2001 |
| JP | 20011283839 A | 10/2001 |
| JP | 2002280056 A | 9/2002 |
| JP | 2002338111 A | 11/2002 |
| JP | 2003065966 A | 3/2003 |
| JP | 2003215051 A | 7/2003 |
| JP | 2004022206 A | 1/2004 |
| JP | 2004200012 A | 7/2004 |
| JP | 2004212159 A | 7/2004 |
| JP | 2006179322 A | 7/2006 |
| JP | 2006275793 A | 10/2006 |
| JP | 2006275794 A | 10/2006 |
| JP | 2007012357 A | 1/2007 |
| JP | 2008153119 A | 7/2008 |
| JP | 2008170197 A | 7/2008 |
| JP | 2009176648 A | 8/2009 |
| JP | 2009277562 A | 11/2009 |
| JP | 2010015777 A | 1/2010 |
| JP | 04509840 B2 | 7/2010 |
| JP | 2010257861 A | 11/2010 |
| JP | 04621524 B2 | 1/2011 |
| JP | 2011064526 A | 3/2011 |
| JP | 04899313 B2 | 3/2012 |
| JP | 2012174388 A | 9/2012 |
| JP | 2012221713 A | 11/2012 |
| JP | 05240830 B2 | 7/2013 |
| JP | 05250320 B2 | 7/2013 |
| JP | 05412221 B2 | 2/2014 |
| JP | 05701639 B2 | 4/2015 |
| KR | 1020070085908 | 8/2007 |
| KR | 1280068 B1 | 6/2013 |
| KR | 20130137228 A | 12/2013 |
| KR | 20130137230 A | 12/2013 |
| WO | WO 0107901 A1 * | 2/2001 ............. G01N 25/72 |
| WO | 2012137902 A1 | 10/2012 |
| WO | 2012137926 A1 | 10/2012 |
| WO | 2013000570 A1 | 1/2013 |

* cited by examiner

THERMOGRAPHY FOR BATTERY COMPONENT QUALITY ASSURANCE

CROSS REFERENCE TO RELATED APPLICATION

This application is a 371 application of international application Serial No. PCT/US2012/061944, which claims priority to U.S. Provisional Patent Application Ser. No. 61/551,193, filed Oct. 25, 2011, all of which are incorporated herein by reference.

GOVERNMENT RIGHTS

This invention was made with government support under Contract No. DE-EE0002494 awarded by Department of Energy. The government has certain rights in the invention.

FIELD OF THE INVENTION

Various embodiments of the present invention pertain to improvements in detection of defects during manufacturing processes, and in particular to detection of defects in the fabrication of batteries.

BACKGROUND OF THE INVENTION

Lithium-ion batteries are an increasingly important power source for small and large scale energy storage applications, including portable devices and vehicles. However, their cost of production remains high, they can have significant degradation over the product life-cycle and there have been some catastrophic failures. Improvements in the battery's manufacturing process can provide cost-saving, improve life-cycle performance and enhance safety. Many battery technologies use a similar manufacturing process that involves coating of anode and cathode materials on a metallic film; thus, improvements in the manufacturing process could affect a wide range of current and future battery chemistries.

Significant flaws in a battery can sometimes be detected immediately after manufacturing during the conditioning period and initial testing of the battery, where the cost is just the lost time and materials for that one battery. More problematic are minor flaws that can go undetected, but overtime lead to a loss of capacity that can result in warranty returns and may in some cases have long term safety consequences. For example, if the Li-ion batteries in a PHEV do not meet the life performance warranty, the whole car which is built around the battery may have to be returned with devastating financial impact. In addition to a loss in capacity, flaws in electrode materials can lead to imbalances of charge states upon charging and discharging and can lead to some cells overcharging and overdischarging, leading to potential safety concerns associated with unsafe voltage regimes. Unsafe voltage regimes can be characterized by formation of gases, and if the battery is somehow damaged to expose the cells to moisture and oxygen, can cause explosive reactions. Thus, manufacturing integrity is important not only for warranty repairs but also for the well being of consumers of the batteries.

In order to mitigate some warranty and safety concerns, Li-ion batteries are currently only used at approximately 30% of full capacity. If the manufacturing process could be improved so that just 40% of full capacity could be used, this would result in a ⅓ increase in the effectiveness of these battery using existing chemistry. Considering the tens of billions of dollars in current production of large format Li-ion batteries, even modest improvement in manufacturing technology can have good payoff.

What is needed are improvements in the processes used to detect manufacturing flaws before the battery is assembled. Various embodiments of the present invention do this in novel and unobvious ways.

SUMMARY OF THE INVENTION

Various embodiments of the present invention pertain to the inspection and monitoring of thin film devices during the fabrication process.

One aspect of the present invention pertains to a method for monitoring a process for manufacturing batteries. Some embodiments include providing a thin film battery component, a source of energy, and a radiation imaging sensor. Other embodiments include pulsing energy from the source onto the thin film battery component and detecting radiation with the sensor emitted from the thin film battery component.

Another aspect of the present invention pertains to a system for monitoring a process for manufacturing a thin film battery component. Some embodiments include a sensor providing a signal corresponding to the temperature of the film of the thin film battery component. Other embodiments include an actuatable source of radiation capable of emitting radiation in a short pulse and directed at the thin film battery component. Still other embodiments include a computer having memory and software and being operably connected to the source, the computer preparing data in memory corresponding to the signal.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting.

DESCRIPTION OF THE PREFERRED EMBODIMENT

Figure 1A:
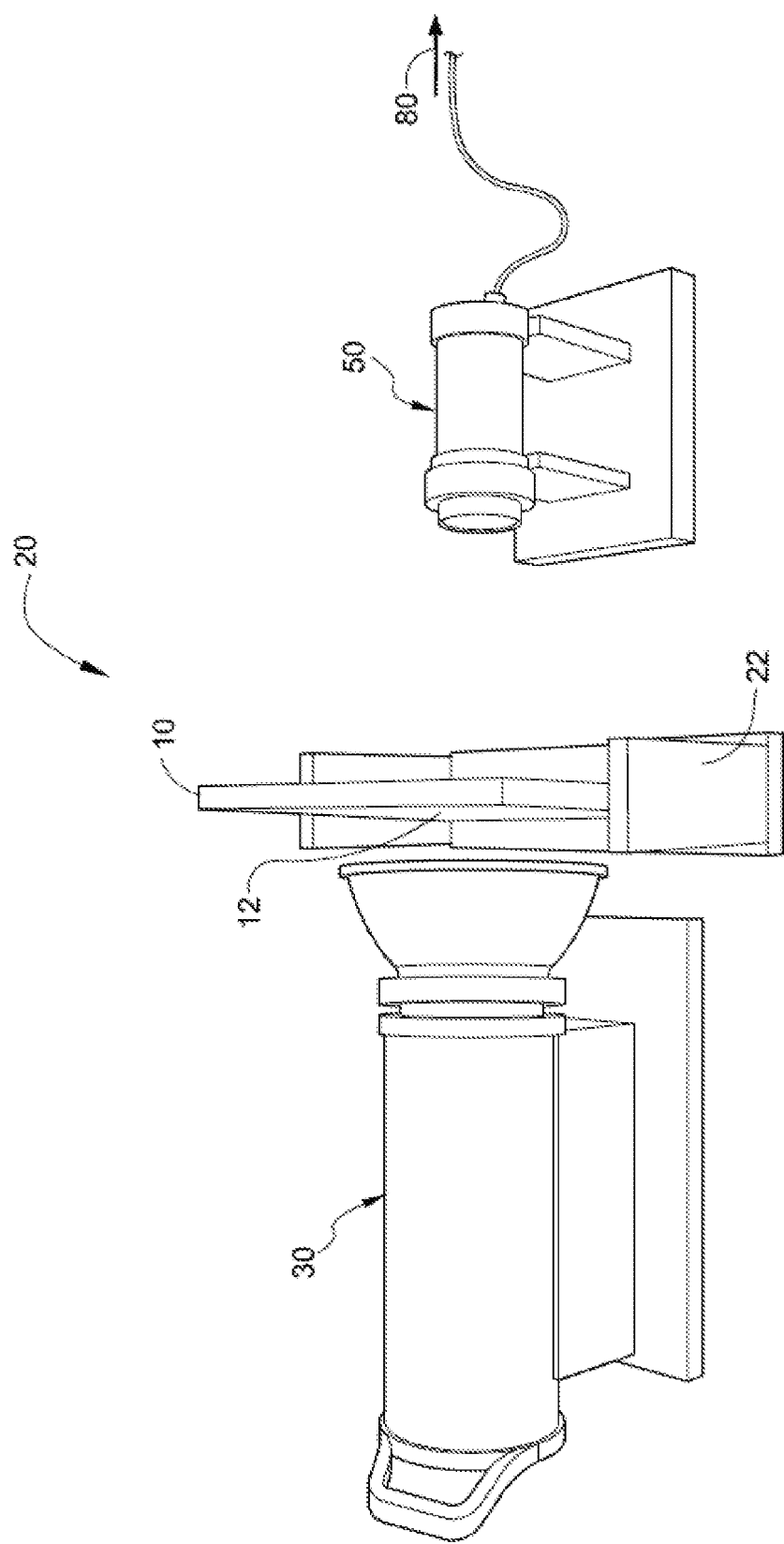
FIG. 1A is a photographic representation of a setup for detection of coating flaws, according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims.

The use of an N-series prefix for an element number (NXX.XX) refers to an element that is the same as the non-prefixed element (XX.XX), except as shown and described thereafter The usage of words indicating preference, such as "preferably," refers to features and aspects that are present in at least one embodiment, but which are optional for some embodiments. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. This description convention also applies to the use of prime ('), double prime ("), and triple prime ('") suffixed element numbers. Therefore, it is not necessary to describe the features of 20.1, 20.1', 20.1", and 20.1'" that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

What will be shown and described herein, along with various embodiments of the present invention, is discussion of one or more tests that were performed. It is understood that such examples are by way of examples only, and are not to be construed as being limitations on any embodiment of the present invention. It is understood that embodiments of the present invention are not necessarily limited to or described by the mathematical analysis presented herein.

The flash thermography technology described herein can improve manufacturing effectiveness by providing, in one embodiment, rapid monitoring of anode and cathode films during the manufacturing process prior to assembly of the films into a battery, which will reduce variability and the likelihood of premature cell failure. Various embodiments include sensing technology that is capable of rapidly detecting composition differences as low as 2% and thickness differences as small as 3% or less. The technology is robust and rapid, enabling the inspection of the anode/cathode components on time scales consistent with automated production of batteries.

Various embodiments of the present invention pertain to the use of flash thermography in the detection of various flaws, defects, dirt, debris, and other unwanted inconsistencies in the manufacturing of a thin film device. As one example, various embodiments are applicable for use in the quality assurance of thin film devices such as anodes and cathodes used in metallic ion batteries. Yet other embodiments pertain to other applications, including the manufacture of solar panels that include thin-film components. Yet other embodiments are applicable to the inspection of members that are painted, or otherwise coated.

In one embodiment, there is a method for monitoring a process for the fabrication of the thin-film device which includes applying a pulse of energy on one side of the component, and mapping the transient thermal response of the other side of the component. In one method the pulse of energy is applied to a substrate (such as a thin plate or foil), and the thermal response is measured of a coating applied to the substrate. However, in yet other embodiments the pulse is applied to the coated side, and the response is measured from the uncoated (substrate) side. In still further embodiments, the method is applied to a thin plate or foil that is uncoated.

In some embodiments, the response of the thin film device is measured as it is being manufactured on a substantially continuous (or very long) substrate, with the coating being applied to the long substrate. In yet other embodiments, the response of the thin-film device is measured after the coated substrate has been severed into a configuration of suitable length for the end product (such as the battery or the solar panel). Still further embodiments pertain to the measurement of the response of the thin-film device during a batch process, or to individual pieces (such as those that would be pulled from an inventory room). In some embodiments the term "thin" refers to a substrate having a thickness that is at least one order of magnitude smaller than either the width or the length of the substrate. In yet other embodiments the thickness is about 2 orders of magnitude (or a factor of 100) smaller than either the width or the length. More preferably, the thickness is about three orders of magnitude (or factor of 1000) smaller than either the width or the length.

In those embodiments in which the thickness is substantially smaller than either the width or length, the thermal response of the device to a short pulse of energy is substantially one-dimensional for a short period of time following the pulse. Therefore, the thermal response that can be measured on the side opposite of the radiant input will be largely a function of the thermal conductivity and the thickness of the device. Therefore, if either the substrate or the coating have a variance in thickness, then the transient temperature profile will likewise reflect this variance. Thinner areas of the thin film device will conduct heat more quickly, and therefore appear hotter for a brief time on the side of the device opposite the radiant input. Therefore, the planar surface of the device will exhibit a response showing the variation in the coating temperature in the lateral (X and Y, or length and width) directions.

After sufficient time has elapsed, however, these gradients will largely disappear as heat transfer occurs in the lateral directions. For the example of a thin-film device with high thermal conductivity, the substantially non-uniform thermal response appearing immediately after the pulse will dissipate to a substantially uniform temperature in the X and Y directions, such that the only gradients observable may be due to edge effects or the like.

Preferably, the initial, transient one-dimensional thermal response is initiated by a pulsed source of energy. In some embodiments, the source emits energy having a pulse with less than about one tenth of a second, less than about ten milliseconds in yet other embodiments, and preferably less than about 5 milliseconds in some embodiments. In some embodiments, the source is pulsed a single time, and one or more response measurements are subsequently made of the device. Preferably, the first measurement is made at a short time interval or delay after the cessation of the pulse, this duration being sufficient to permit a distinguishable gradient to be measured, but not so long as to have the gradient laterally dissipate.

This short time interval can be considered in terms of the one-dimensional heat transfer time constant for the thin-film device, although various embodiments the present invention are not so limited. As one example, there is a delay in measurement of the response after the pulse is ended of about one time constant. It is further appreciated that the parameters that establish this time constant (including thermal conductivity and thickness) or variable within the manufacturing process of the thin-film device. As one example, it may be permissible to have the thickness of the metallic foil vary by + or −10%. As another example, the thermal conductivity of the coating material may vary by + or −10%. Therefore, it is preferable to select the interval to take into account the potential range of acceptable thermal time constants.

Governing equation for the temperature is one-dimensional transient heat transfer given by $$\frac{\partial T}{\partial t} = \alpha \nabla^2 T \alpha \quad (1)$$

where $\alpha = k/\rho C_p$ is the thermal diffusivity given in terms of the thermal conductivity k, the density $\rho$ and the specific heat capacity of the material $C_p$. Scaling Eqn. 1 yields the relationship between the characteristic time $\tau$ of the transient heat transfer process and the characteristic length, i.e. the film thickness and $\chi$; specifically, $$\tau = L^2/\alpha \quad (2)$$

Now consider a coated film with areas of different thickness or composition (the composition affects $\chi$; By Eqn. 2 there will be a different characteristic times. If the backside of the surface is exposed to a short flash of energy, then a schematic of the evolution of the surface temperature is shown in FIG. 1 for three different regions of the thin film. The film area that is thinner (or has higher $\chi$) will have a smaller $\tau$ and consequently the surface temperature will rise first. Conversely, the film area that is thicker (or has lower $\chi$) will have a larger $\tau$ and consequently the surface temperature will rise later.

Figure 1B:
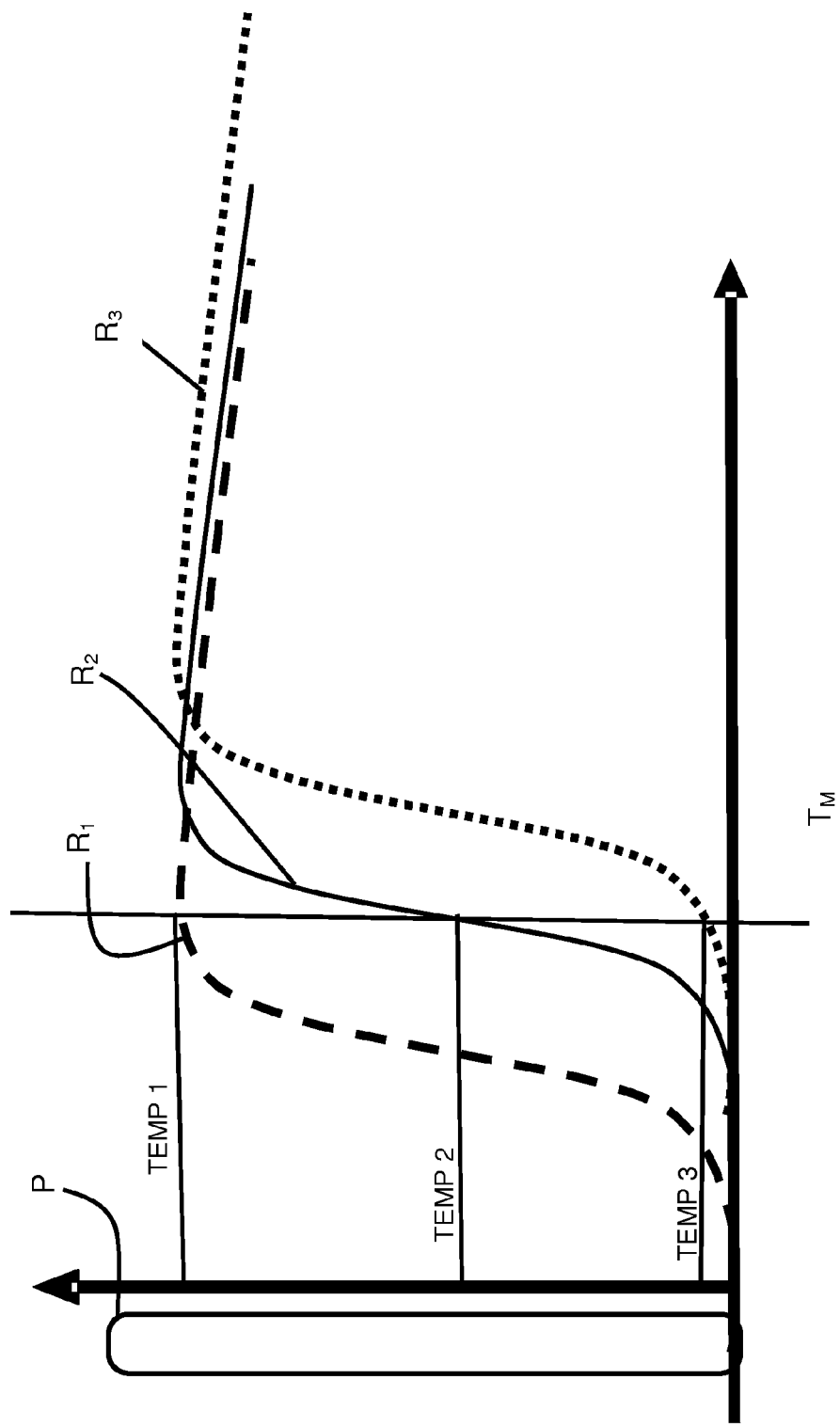
FIG. 1B is a graphical representation of an energy input and a thermal response according to one embodiment of the present invention.

Referring to FIG. 1B, there is shown a graphical time-based representation of an input pulse P and subsequent thermal responses R1, R2, R3. A short duration pulse P is applied to a side of the thin film device. In one embodiment, pulse P has a width of anywhere from about 2-4 milliseconds. A short time after that pulse P from source 30 is applied, the thermal response of a side of the thin film device is measured by detector 50. FIG. 1B shows that areas of the film having different time constants will indicate different temperatures at any time during a transient period and before the dominoes of steady state effects. For example, for a measurement made at time Tm, an area of the thin film device having a short time constant (as represented by curve R1) will show a relatively high temperature (TEMP 1). A region of the thin film device with a longer time constant (region R2) will indicate a lower temperature (TEMP 2). Finally, those regions R3 of the device with the longest time constants will indicate the lowest temperature (TEMP 3).

Detector 50 will therefore send a signal to computer 80 at time Tm that will be detected as data indicating different temperatures in these three regions. Subsequent data processing software will manipulate this data to assess this thermal gradient in both spatial and temperature aspects to determine if the gradient is indicative of a manufacturing inconsistency.

Figure 1C:
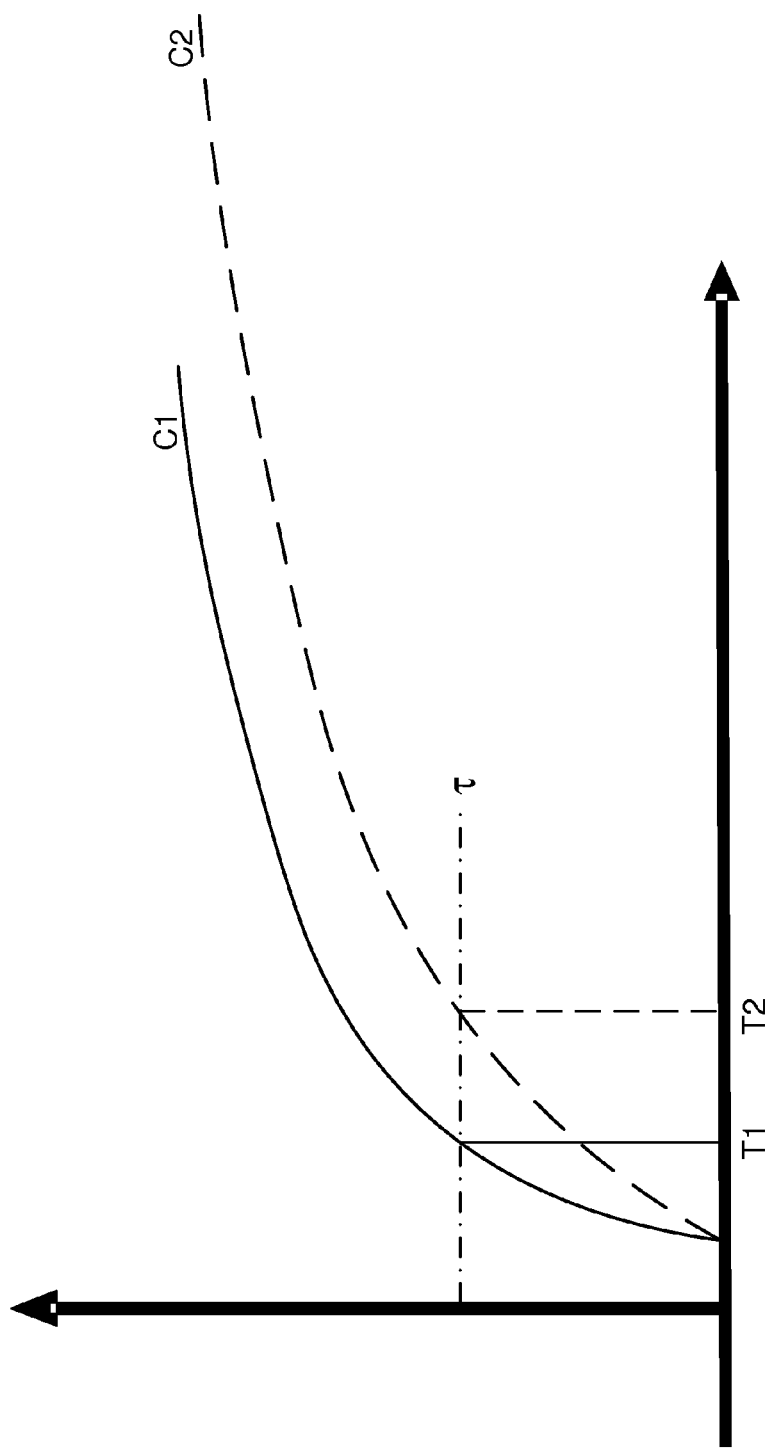
FIG. 1C is a graphical representation of thermal responses according to one embodiment of the present invention.
Figure 2A:
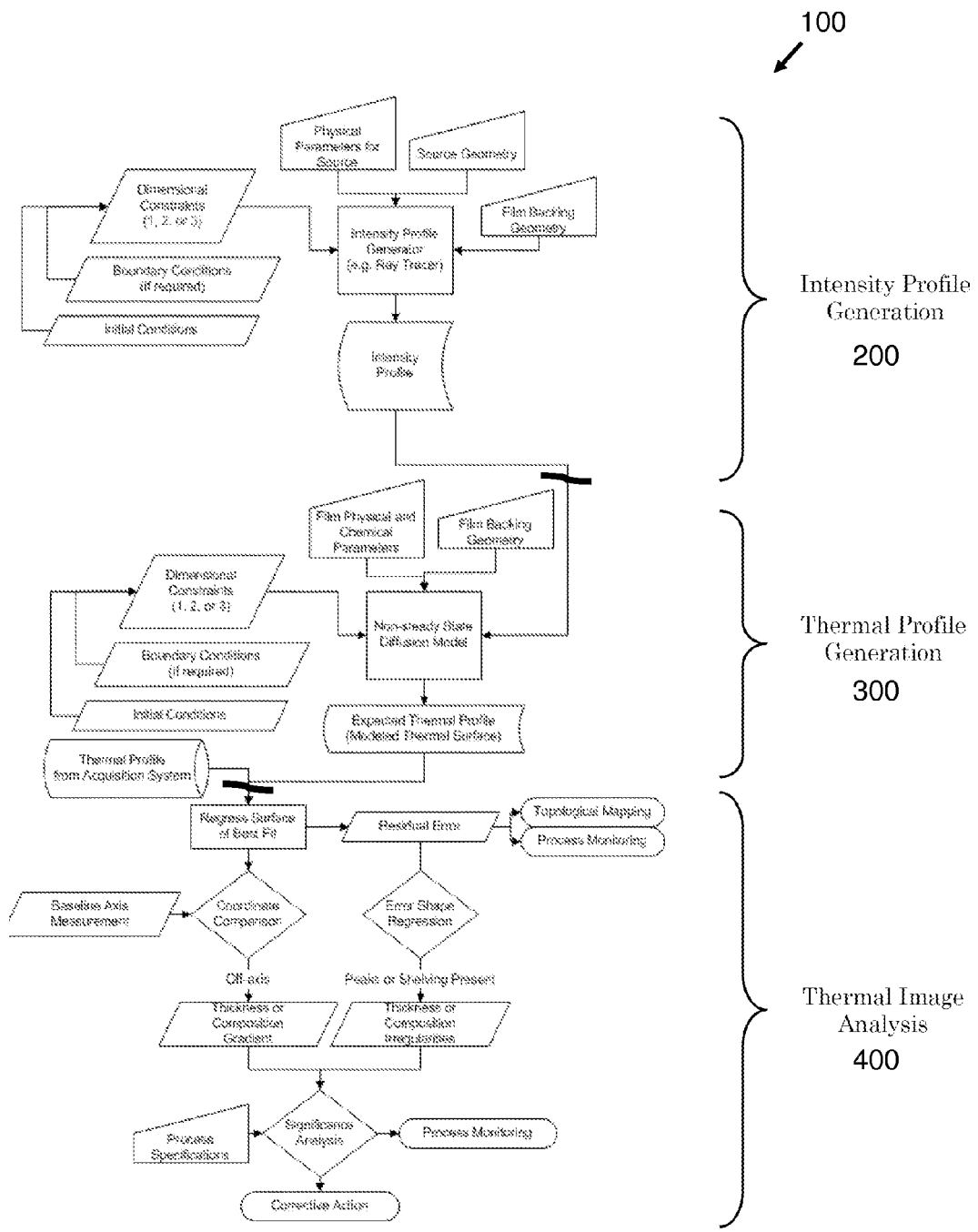
FIG. 2A is a flowchart showing thermal defect detection and quantification according to one embodiment of the present invention.
Figure 2B:
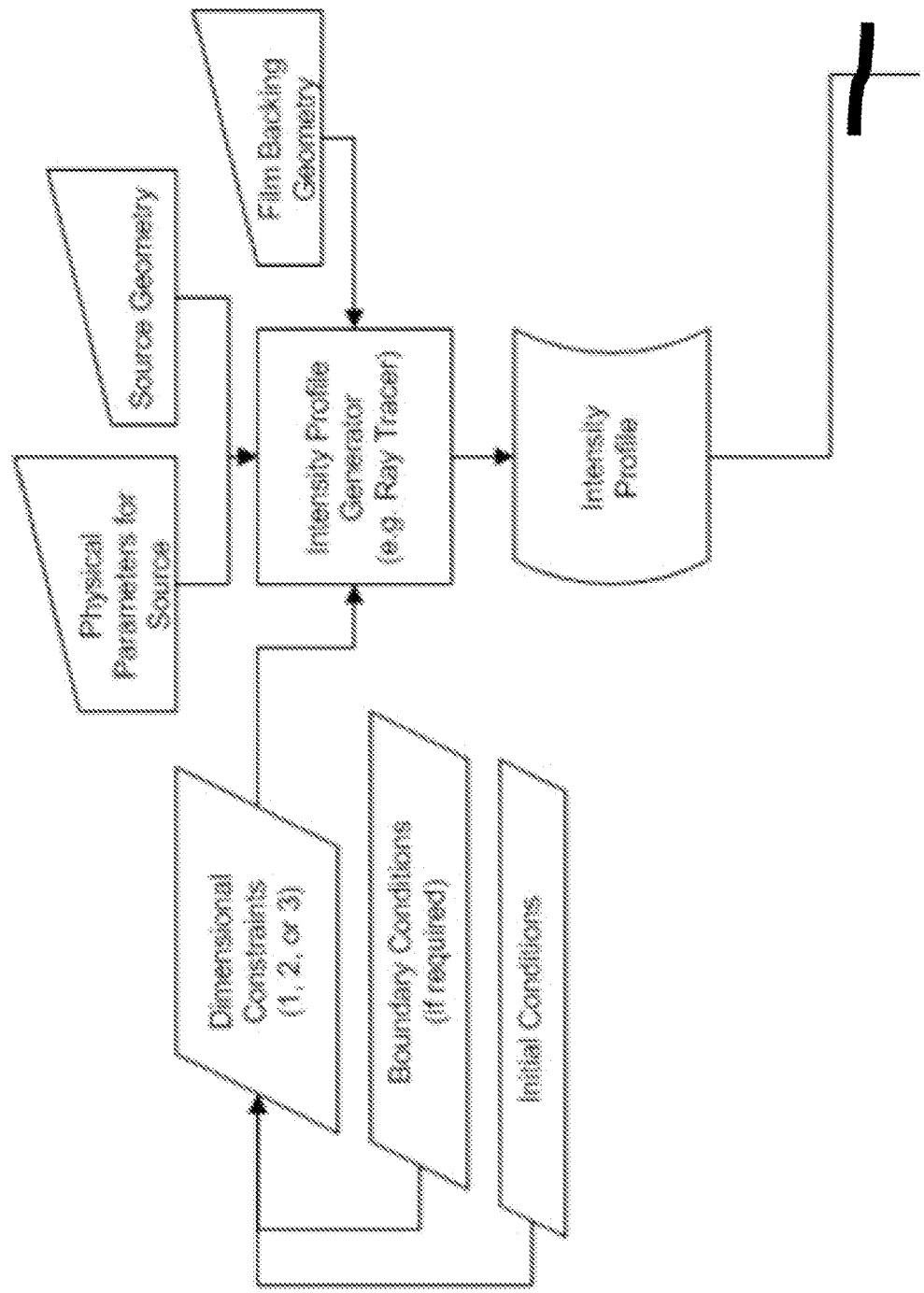
FIG. 2B is an enlargement of a portion of the flow chart of FIG. 2A.
Figure 2C:
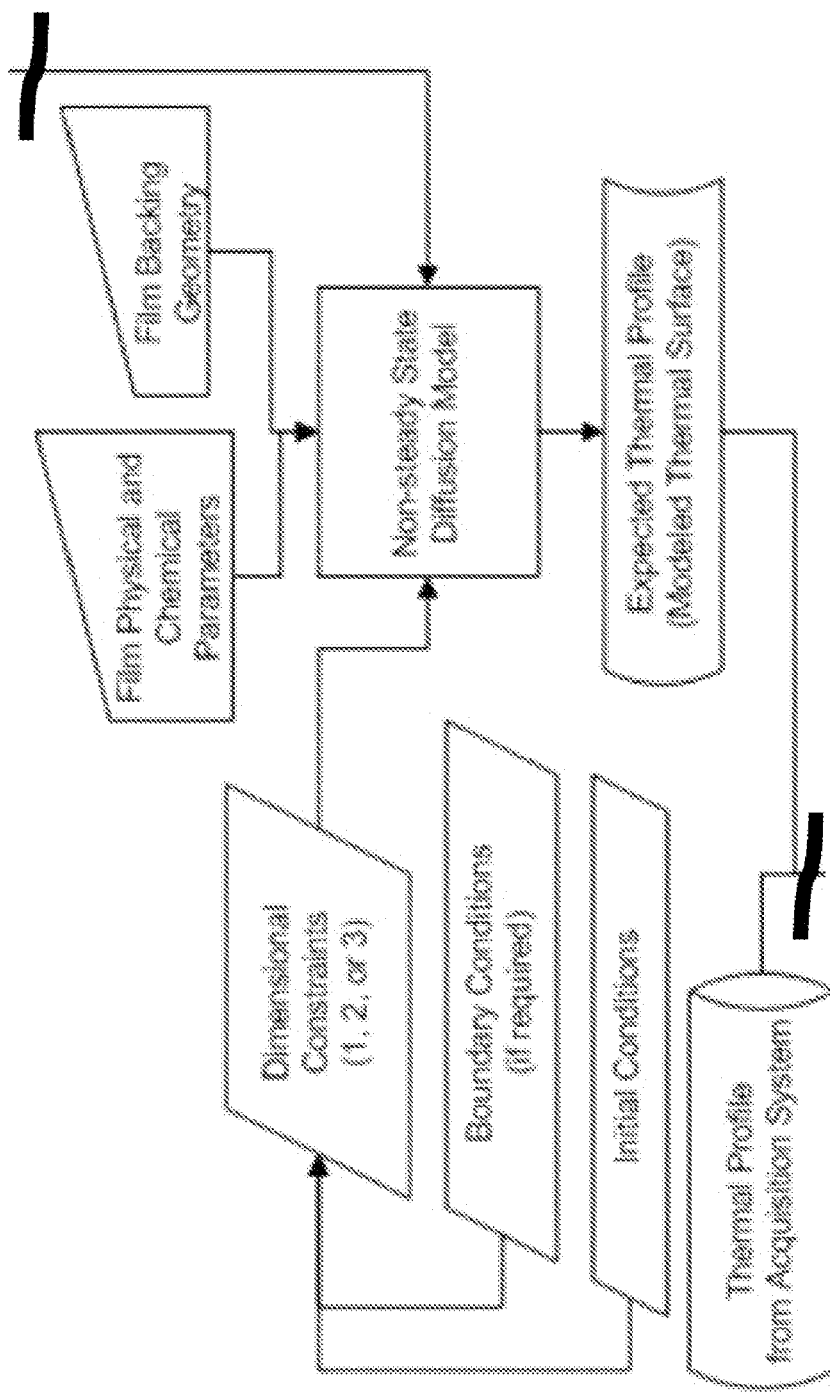
FIG. 2C is an enlargement of a portion of the flow chart of FIG. 2A.
Figure 2D:
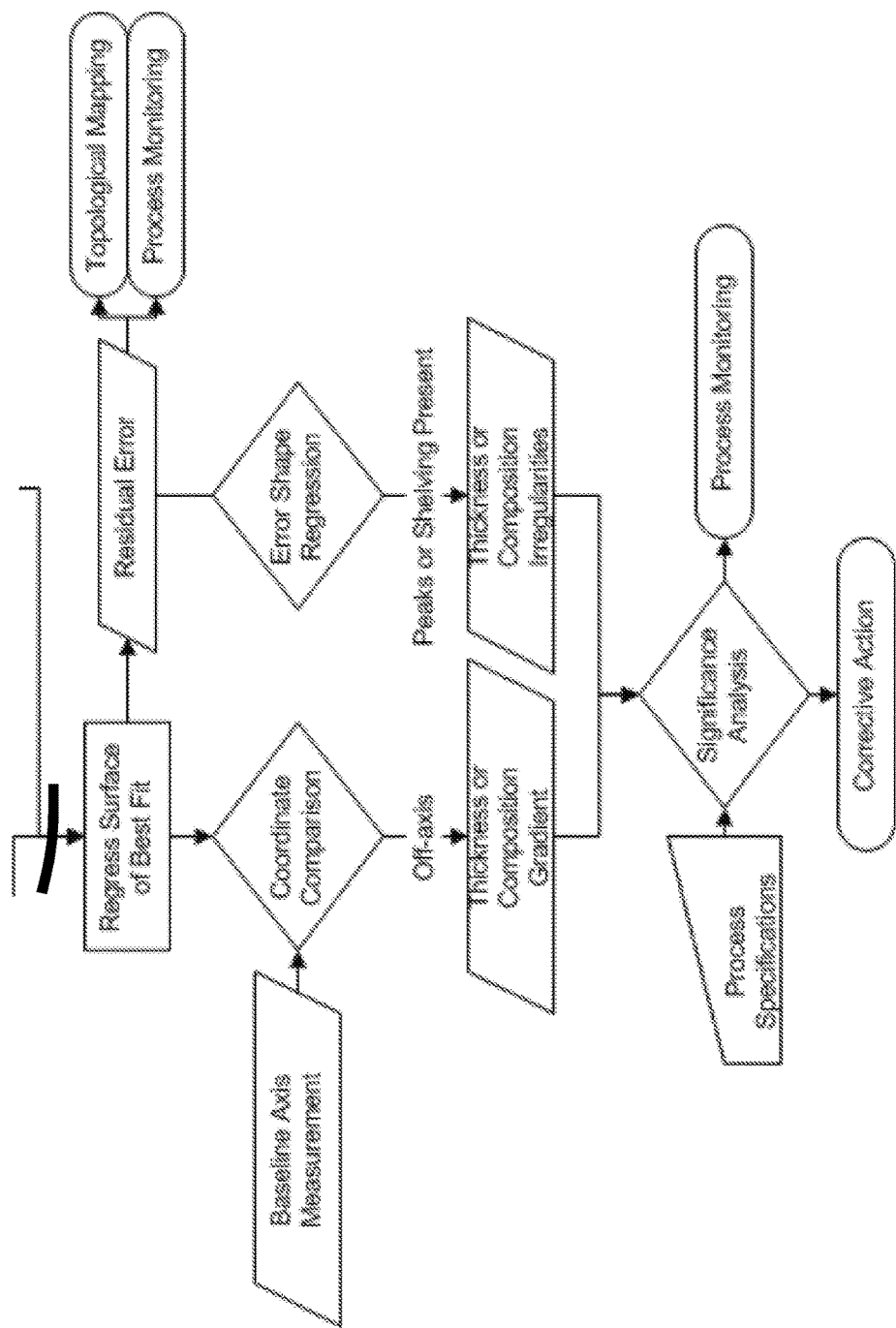
FIG. 2D is an enlargement of a portion of the flow chart of FIG. 2A.

FIG. 1C graphically depicts responses from two thin film components C1 and C2. For purposes of clarity, the thermal responses are normalized to the same range of minimum to maximum. However, it can be noted that thin film component C1 (such as a battery component) has a faster time constant than thin film component C2 (such as a solar panel component). Therefore, in those embodiments in which the measurement is taken at a time generally representative of the first time constant of response, component C1 would be measured at a time T1, and component C2 would be measured at a time T2.

Referring again to FIG. 1B, it can be seen that after the initial temperature rise extends to its peak value, the temperature of the hotter portions decreases, which is the dissipation effect as the high temperature locations transfer heat in lateral directions. Likewise, on portions of the thin-film component having very low thermal conductivity (or very high thicknesses), there may be no peak initial temperature, and instead the temperature in such slow to respond regions simply increases monotonically and asymptotically to a final value.

In various embodiments of the present invention there are various temporal relationships established in the measurement system that relate to the thermal response characteristics of the device being measured. As one example, in some embodiments the thermal response data is collected by the computer before a period of four time constants (4 TAU) have transpired. In these embodiments a delay beyond about 4 TAU results in excessive dissipation of the transient one-dimensional gradient into the two other spatial directions. And yet other embodiments, it is noted that it can be useful to begin acquisition of the transient thermal response data at least one time constant (TAU) after the energy pulse has ended. By waiting at least for one time constant, it is possible that the one-dimensional thermal gradient will be expressed with more than half of the peak temperature. In yet other embodiments having two measurements made of the component, it is preferable that the two measurements be separated by a sufficient period of time such that additional, relevant thermal information about the component is revealed. In such embodiments, it is preferable that there be a time interval of more than about one time constant between the initiation of the first measurement, and the initiation of the second measurement. As yet another example, it is useful in some embodiments to utilize a source of energy having a pulse width that is less than about one time constant. In such embodiments it is possible that excessively long pulse durations apply to much heat to the component being tested, with subsequent loss of resolution in the transient data.

After capturing a thermal image, various embodiments utilize digital signal processing of the sensor signal to identify regions of the thin-film device that are suspected to be deficient and rejectable, or simply usable in a final device having lesser performance. These embodiments can employ a computer with software and memory that is operably connected to the source of energy (so as to actuate a pulse), and receiving an electronic signal from the sensor. The signal is transformed into a three-dimensional map of the device surface, with two of the dimensions being spatial in nature, and the third dimension being temperature information.

This three-dimensional map can be processed in a variety of ways, as discussed further herein. As one example, a best fit plane can be identified in the data, and the difference between the data and the plane can be utilized to more easily show defects and inconsistencies. As another example, the data can be compared to one or more representations of acceptable devices (product baselines). These baselines can reside in computer memory, or they may be reestablished on a periodic basis (using product samples) to take into account any shifts or inconsistencies in the thermal gradient detection process (such as changes in the intensity of the pulsed source, changes in the sensitivity of the sensor, changes in the location of the sensor, and the like).

As yet another example of signal processing, in some embodiments a second thermal image of the device is captured by the software after the first image has been acquired, and before the one-dimensional thermal gradients have dissipated in the length or width of the device. As one example, the second thermal image may be captured at the end of an interval following the capture of the first image, such as an interval of about one time constant. In such a system, the first and second thermal images will be captured at about the completion of the first and second time constants, respectively. The first image can then be compared to the second image for improved detection of suspect regions of the device, or further for identification of the possible type of defect.

Various embodiments of the inventions described herein are applicable to various stages of fabrication of the thin-film device. As one example pertaining to a cathode or anode, the various methods of detecting the thermal gradients of the device can be used: (1) immediately after the coating has been applied; (2) after the coating has been allowed to dry; (3) before the coating has been compacted; (4) after that the coating has been compacted; (5) or the like. In still further embodiments, the fabrication process includes a station immediately prior to the station at which the thermal gradient is measured, this station being adapted and configured to provide a baseline condition to the device before the gradient is measured, and therefore provide improved consistency and repeatability in the gradient measurement method. As one example, there can be a station prior to the gradient measurement station in which clean air is directed at the coating surface, so as to remove loose dust or debris. As another example, the station can include a source of control heat (or controlled cooling) so as to provide a repeatable baseline temperature prior to the gradient measurement.

Still further, although what will be shown and described is a method in which a pulse of energy is applied to one side of an object and the thermal response is measured from the other side, yet other embodiments are not so constrained. As one example, some embodiments include the application of an energy pulse and also the measurements of a thermal response from the same side of a plate or foil. In some of these embodiments the pulse of energy is applied in a first electromagnetic spectrum, and the response spectrum of the sensor occurs in a second electromagnetic spectrum that is substantially different than the first spectrum. In still further embodiments the pulse of energy can be characterized as having a peak intensity at a first wavelength, whereas the sensor measuring the response of the object has a peak sensitivity and a second, different wavelength that is sufficiently separated from the first wavelength.

Lithium-ion secondary batteries produce power by the migration of lithium ions from an anode electrode to a cathode electrode. The cathode and anode include a thin current-collecting metal foil backing (usually aluminum or copper) and a thin film coating of the active material. The coating of the cathode is typically a lithium/metal oxide, while the anode is usually coated with conductive graphite. A cell is composed of a cathode, an anode, a porous separator layer between the anode and cathode, and a lithium-ion electrolyte solution that carries the charge between the anode and cathode. Lithium ions shuttle back-and-forth between the anode and cathode, and they are inserted into the active material by a process termed intercalation. The specific materials used in the coatings determine the voltage of the battery. Most lithium-ion system chemistries produce potentials of between 3.6 to 4.2 volts when fully charged.

Although various embodiments disclosed herein refer to lithium-ion batteries, it is understood that various embodiments of the present invention are not so limited. For example, the methods and apparatus disclosed for detection of manufacturing defects can be applied to batteries other than lithium-ion batteries, and further can be applied in other applications as will be understood by persons of ordinary skill in the art.

The amount of energy and power that can be produced by a battery depends on its size. Higher capacity is achieved by increasing the number of lithium ions available for migration in the cell by connecting multiple anode/cathode assemblies. Large format Li-ion battery packs contain a very large number of individual cells, where each cell is comprised of numerous pairs of the anode and cathode sheets. In a large application, e.g. the Chevy Volt, there can be in excess of 10,000 sheets, where a flaw in any one sheet can affect the long term performance of the whole battery pack. Because of the low fault tolerance of a large format battery, the manufacturing process for each coating, cell, and battery should be precise.

The process for manufacturing the anode and cathode sheets is a multistep process, where process variability can result in sheets with various types of flaws. Specifically, various powders, solvent and other additives are combined in a large industrial scale mixer creating a concentrated slurry. The slurry is deposited as a thin layer onto a current collector surface in a coating operation. Then the solvent is evaporated in a drying oven at elevated temperatures. Next, the electrode material is compacted to the desired thickness in a two roll mill, where there may be subsequent heating/drying processes. Manufacturer-specific finishing steps may also be performed before the electrodes are cut to size and robotically assembled into the cells that form the battery pack.

Small variations in the manufacturing process can have serious consequences on the resulting anode and cathode films. Some examples include:
1. Less than perfect mixing will lead to material inhomogeneities in the slurry, resulting in composition gradients in the film
2. Imperfections and/or fluttering in the coating blade may lead to thickness gradients
3. Small wrinkles in the underlying metallic film being coated can affect the coating process
4. Spatial temperature gradients in the drying process can affect the resulting microstructure in the anode or cathode material
5. Imperfections such as small scratches or particulates on the two roll mill used during compaction can result in imperfections in the resulting anode/cathode films
6. During the cutting process, small metal flakes may contaminate the film
7. Other process flaws However, because of the large number of anode/cathode sheets present in a large format battery pack even flaws at less than 1 per million can have serious consequences.

The development of a method to detect the various manufacturing flaws described above could impact Li-ion battery manufacturing. Moreover, since other battery technologies, e.g. silver-zinc, also use similar coating/drying/compaction/assembly processes, as examples, this sensing technology would have application in these manufacturing processes. Optical detection of flaws at production line speed is difficult, because flaws are often difficult to see even upon close examination due to the dark color, smooth texture, and matte quality of the coated films. Topological laser detection faces challenges because carbon present in the material will fluff and prevent reliable depth measures.

The results presented herein indicate that high-speed thermographic imaging can identify manufacturing defects in the anode and cathode sheets used in lithium-ion batteries, before the materials are further processed for battery pack assembly. A variety of undesirable film qualities can be readily detected, including pinholes, thickness gradients, composition differences, bubbles and droplets, striations, and backside contaminants. When the imaging is combined with intelligent signal processing algorithms, quantitative results can be achieved. Flash thermography can be implemented as an on-line process for continuous product quality tracking, either just prior to the robotic cell assembly process or during the film manufacturing process before and/or after the compaction operation. Although the data shown in this communication were for Li-ion based battery materials, the techniques are generally applicable to a variety of film coating operations, including battery chemistries other than Li-ion as well as polymeric and other material films.

A thermographic imaging system 20 according to one embodiment of the present invention is shown in FIG. 1. A sample 10 containing the film of interest is mounted between a flash bulb 30 and a thermal camera 50 with the metal foil side 12 facing the flash. The flash energy source 30 is activated, which provides a burst of energy to the foil. A barrier 22 surrounding the mount prevents energy not transmitted directly through the sample from reaching the camera's view, and the apparatus is covered to reduce effects due to ambient light. In yet other embodiments, additional sensors and signal processing can be added to compensate for ambient effects.

In some embodiments, a camera and appropriately placed sensor can provide real time information about the reflectivity of the side of the film being exposed to the flash energy. In so doing, changes in the plate materials (such as plates received from alternative venders) that have reflectivity variations can be detected and compensated for during the flash measurements. In addition, it is possible to take measurements from the same side of the film as the flash sensor, and before (upstream) of the flash sensor, in order to note any variations in ambient radiant conditions within the wavelengths of interest.

The thermal camera records the thermal profile of the film coating as the energy diffuses through the sample. Because the films are thin, the transient effects are rapid and approach their asymptotic values within seconds. The thermal camera is sampled at a high frame rate to capture the thermal diffusion. This setup is orientation-independent and can be readily adaptable to a production line environment. The camera connects to a computer 80 running custom image processing software.

Immediately after the flash, the temperature on the foil side of the sample is higher than that of the film side, and because the film thickness is several orders of magnitude less than its width or height, the thermal diffusion through the film is essentially one dimensional. For a material with uniform composition, the time required for the energy from the flash to reach the other side is dependent on the thickness of the material and its thermal conductivity. Conversely, when a material has uniform thickness, composition and porosity differences can introduce departures from an average effective thermal conductivity coefficient, thereby altering the diffusion time. By measuring and analyzing the transient response across the film surface, it is possible to identify and spatially map regions that depart from the expected result or specifications.

The flow chart of an algorithm 100 according to one embodiment is shown in FIG. 2 with three sections: intensity profile generation 200, thermal profile generation 300, and thermal image analysis 400.

The intensity profile from the flash source is computed 100. In the simple case of a flat sheet and uniform source, presented here, it is uniform over the material backing. This leads to a uniform heat flux at the start of the diffusion sequence. A non-steady state diffusion analysis of the material predicts its thermal profile 200 to be uniform across all pixels as well, essentially a plane of uniform temperature. The expected thermal profile 300 is then used as a baseline to analyze the image.

For systems where the simplified case does not produce acceptable results, a non-idealized model of the flash source geometry can be incorporated into the intensity profile to improve the accuracy of the method. Parameters such as the film's specification thickness and a thermal conductivity tensor, if the material is anisotropic, can further improve the thermal profile for image comparison.

Figure 24B:
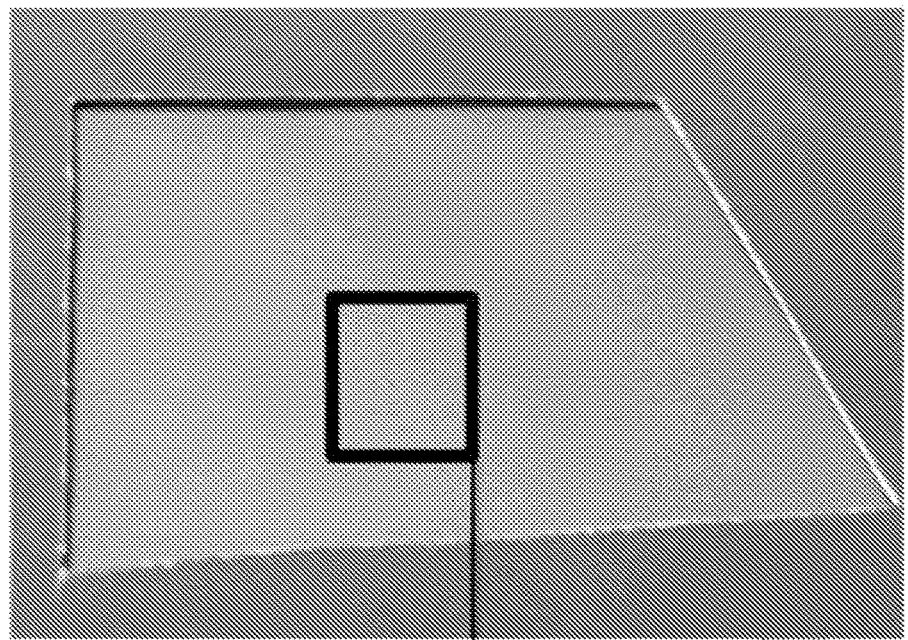
FIG. 24 shows a comparison of film thermograph (a) and photo (b) of droplet detection.
Figure 24A:
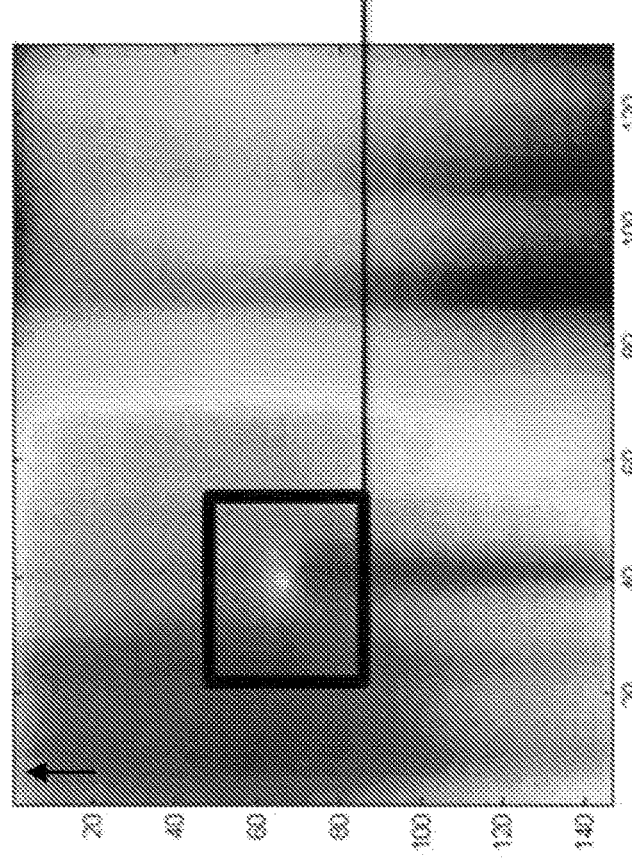
Figure 30:
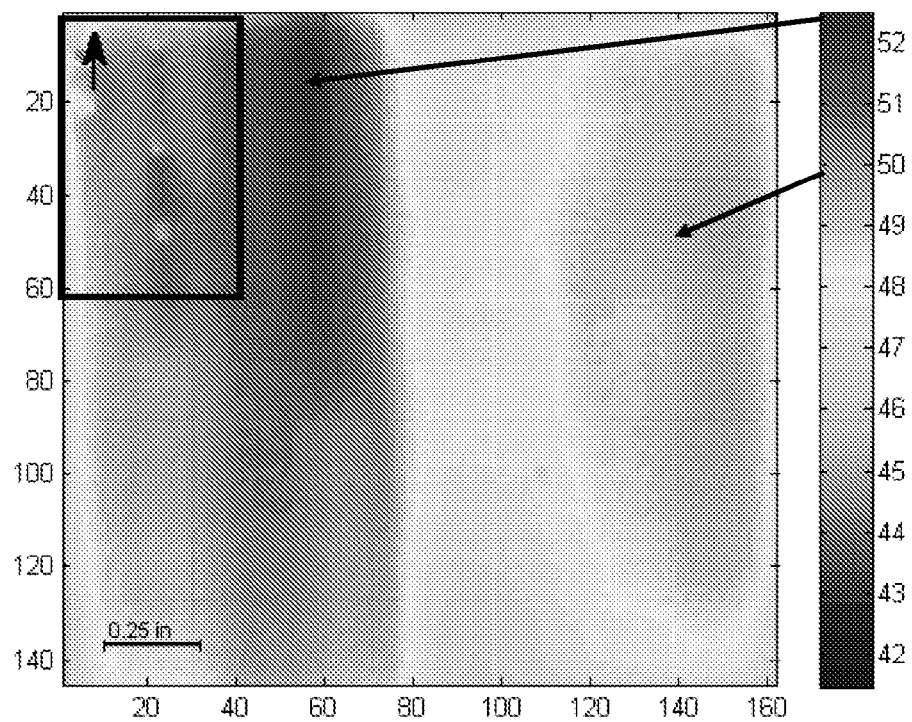
FIG. 30 is a thermograph of a large composition difference of the sample of FIG. 29 according to another embodiment of the present invention.

By analyzing the dynamic response across the film, it is possible to construct a two dimensional map of $\alpha L$ for the coating surface, where $\alpha$ is the local thermal diffusivity and $L$ is the local film thickness. Composition or porosity gradients can affect the thermal diffusivity for the material in question, while thickness variations are expected to result from improperly operating process equipment. Thermal image analysis according to one embodiment proceeds as follows:

1. The thermal response from the sampled image is compared to the expected response which is a flat plane.
2. Deviations from a flat plane image are translated as surface aberrations.
3. The aberrations may be reported as just the raw value from the IR camera or calibrated as an effective thermal thickness" using prior experimental data for the materials under study.
4. The aberrations are to be classified as within/outside of the manufacturing tolerances.
5. By examining their spatial signature using visual signal processing algorithms, the type of flaw can be assigned. Examples include
   a. Dimples may correspond to material droplets (FIG. 24).
   b. Ridges may indicate ripples that result from the coating blade fluttering (FIG. 11) or from thermal deformation during the drying process (FIG. 17).
   c. Composition flaws will appear as plateaus, valleys, or shelves (FIG. 30).

Figure 13:
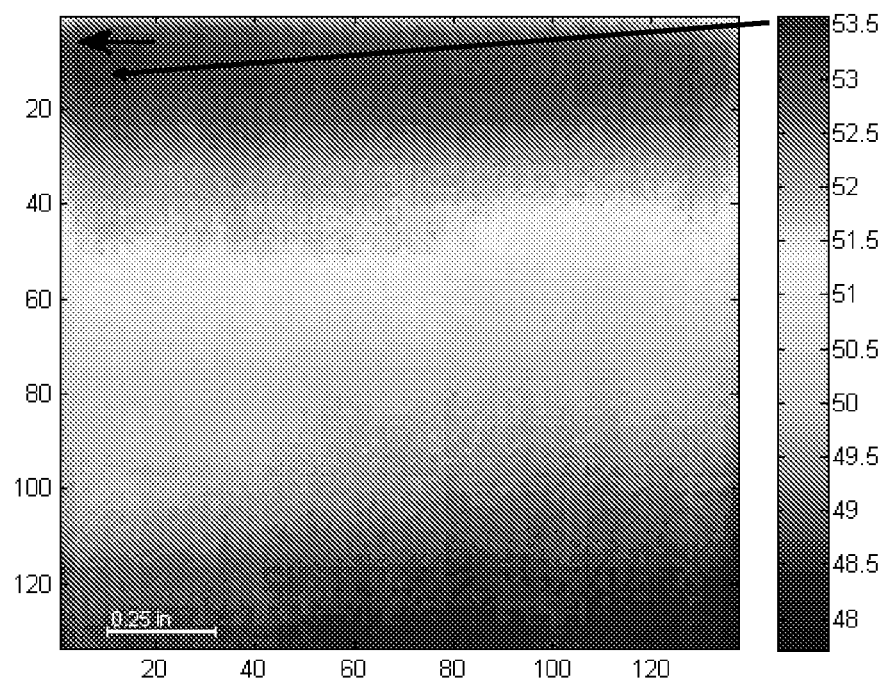
FIG. 13 shows a small thickness gradient (microbolometer thermograph) of the sample shown in FIG. 12 according to another embodiment of the present invention.
Figure 14:
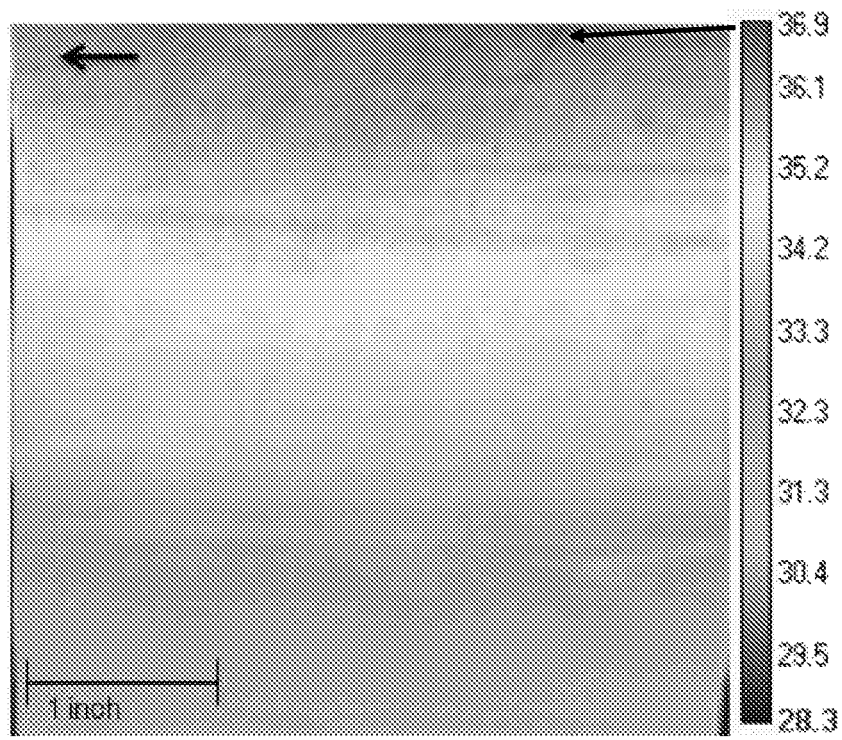
FIG. 14 shows a small thickness gradient (photon detector thermograph) of the sample shown in FIG. 12 according to another embodiment of the present invention.

Since the method measures thermal intensities, higher temperature values for a given sample frame correspond to smaller amounts of resistance, indicating thinner and/or more thermally conductive regions. The plane of best fit for the sample may also be computed and compared against its expected location predicted by the model (a flat plane). A thickness gradient will introduce an angle onto the plane (FIG. 13). This gradient can then be subtracted from the image to analyze for other defects.

If the results of the analysis, which can be performed on-line with the manufacturing process, indicate that an unfavorable process event has occurred, corrective action can be taken immediately, minimizing loss of production time and product. A single frame acquired by the high-speed thermal camera may be used. Analysis of several frames or more will produce results with greater confidence.

Figure 3:
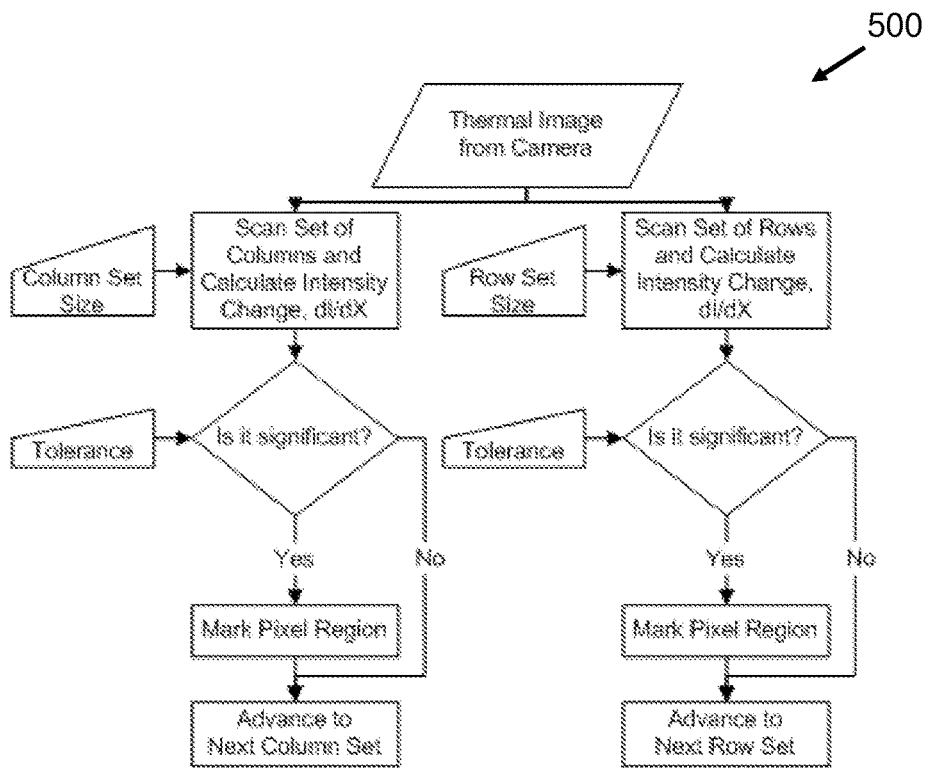
FIG. 3 is a flowchart showing an example of a damage detection algorithm according to one embodiment of the present invention.

A simple defect detection method 500 according to one embodiment is presented in FIG. 3, where analysis is conducted using a single frame of the thermal profile. The thermal response of the image is analyzed for sharp changes along rows and columns of pixels. This method accounts for any planar effects from a camera mounted slightly off-axis. Deviations from the gradient are marked. Calibration using a baseline for the tolerance value aids in detection.

The technology discussed herein is effective for detecting thickness gradients, composition gradients, pimples, pinholes, smudges, underlying metal foil wrinkles, underlying metal foil contaminants, and gross defects on films. The black matte quality of these films makes detection by optical means difficult. The temperature distributions measured by the IR camera are indicated by color, where red is hot and blue is cold and the actual temperature values are given in a scale beside the 2D image. All film thicknesses are in the 50 to 200-micron range. Greater axial dispersion is expected in thicker films and could benefit from two-dimensional modeling in order to capture full information from the flash thermography.

Figure 4:
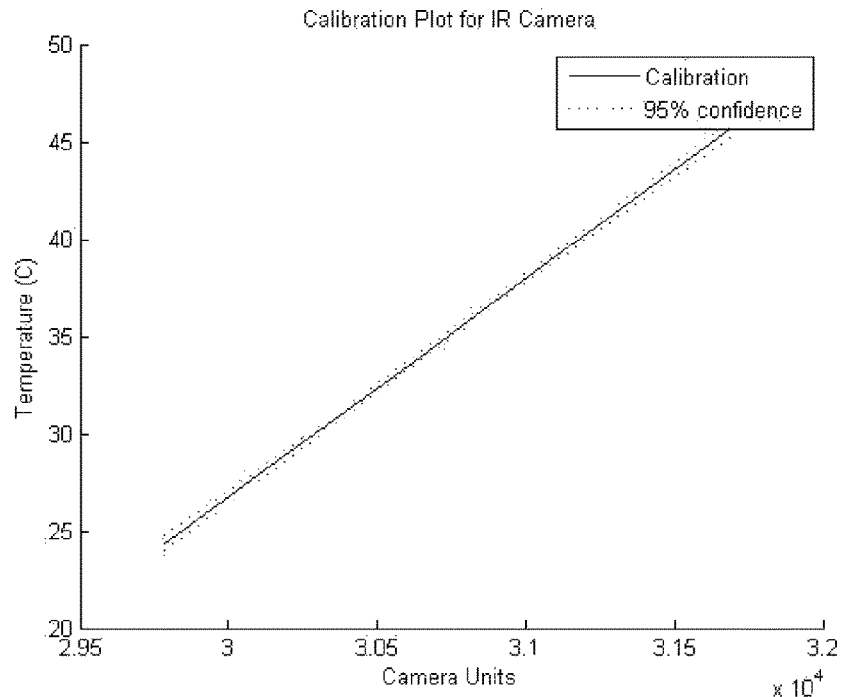
FIG. 4 is a graphical representation of a calibration curve.

Two different types of IR cameras 50 were employed to capture images. One had a photon detector (FLIR SC7650) and a second one operated using a microbolometer detector (FLIR A320). On-board calibration was used with the photon detector-based camera; in contrast, for the microbolometer-based device, data from the camera that was in reported arbitrary units (14-bit unsigned integer) was post-processed into degrees Celsius using a calibration curve. The curve was constructed by placing a film of similar composition and thickness to the ones used (and thus similar emissivity) on a hot plate and raising its temperature slowly and uniformly. A thermocouple was used to determine the surface temperature while the camera recorded data. The resulting curve is linear, as shown in FIG. 4. The 90% confidence limits on the slope and intercept are relatively flat over the range of interest at an accuracy of +0.3° C.

The temperature response was observed between the two camera systems for the flash thermography of the same coated sample. There are two observations: First, the transient process approaches equilibrium in 30 ms which is close to the limit of the maximum 60 Hz sampling rate of the micro-bolometer based IR camera. Second, signal integration in the microbolometer based camera has a time constant of approximately 12 ms and this, combined with its readout method, can cause local smearing of the data and an artificial top to bottom gradient in the recorded images. The artificial thermal gradient observed using the microbolometer camera (see FIG. 7 and associated discussion) can be numerically corrected by using a first order filter that enables defect detection. However, some of the subtler features of the thermographic response may not be discerned using the microbolometer-based camera, in which cases it may be preferable using the fast integration times and higher sensitivity of a photon detector. However, it is understood that various embodiments pertain to the use of any sensor capable of producing an image of the thin film component, or usable in combination with other features of the fabrication process (such as a moving conveyor) to produce an image.

Figure 5:
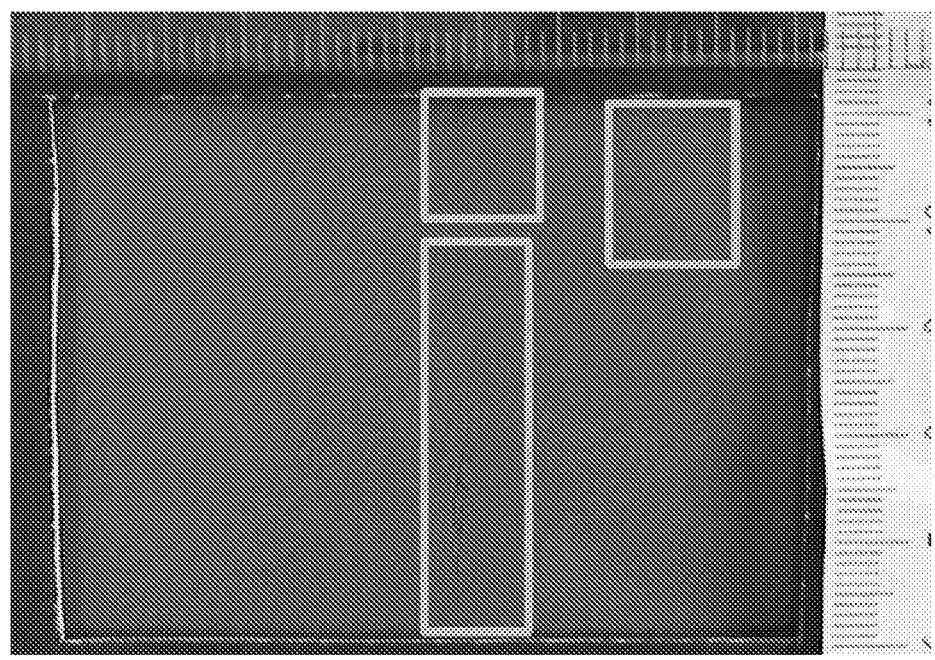
FIG. 5 shows a photo of film with streak and smudge.
Figure 6:
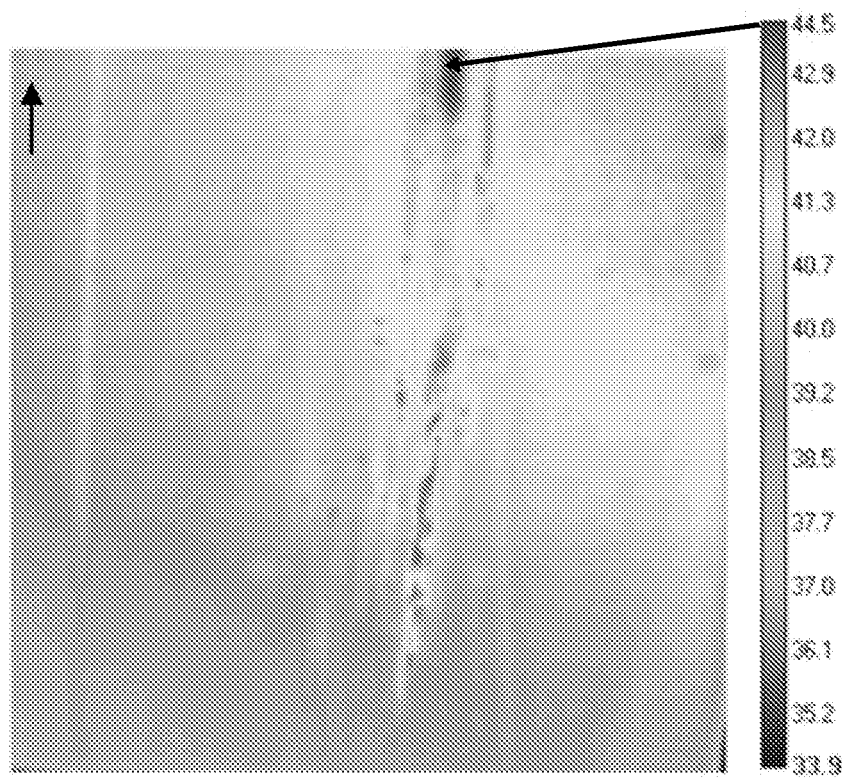
FIG. 6 shows a photon detector thermograph (streak/smudge) of the sample shown in FIG. 5 processed according to another embodiment of the present invention.

FIG. 5 shows an electrode film (anode composed of 80% graphite, 10% PVDF, and 10% carbon black by weight with an approximate film thickness of 70 μm) with a visible streak in the center that can be observed by normal photographic methods and smudges at the top which are invisible to optical cameras, although they are faintly seen upon close visual inspection. FIG. 6 is the image from the flash thermography using the FLIR SC7650 IR camera for the same film shown in FIG. 5. The coater draw direction is indicated in all images by the arrow in the top left corner.

Figure 7:
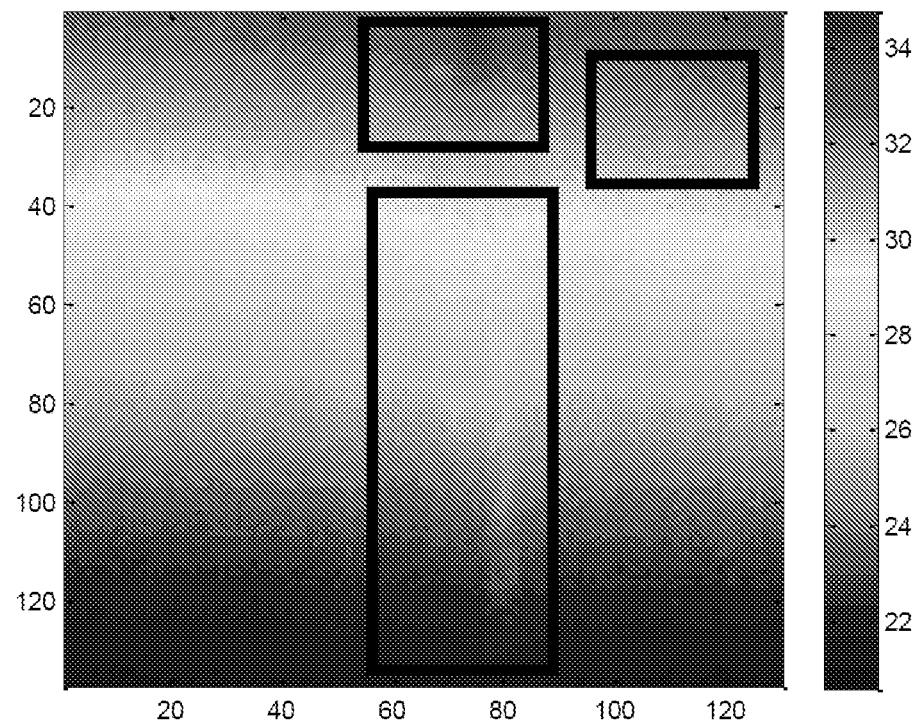
FIG. 7 shows an uncorrected microbolometer thermograph (streak/smudges) of the sample shown in FIG. 5 processed according to another embodiment of the present invention.

The defects in the coated film are evident using the flash thermography method. The thermograph in FIG. 7 is for the same film as in FIGS. 5 and 6, but now the image is recorded with a microbolometer-based IR camera (FLIR A320). The uncorrected thermograph of FIG. 7, taken directly from the microbolometer camera, has a 10 degree C. temperature gradient from top to bottom that obscures the defects (note the dark blue at the bottom corners may be due to edge losses in the film, and possibly not the thermal gradient in the film).

Figure 8:
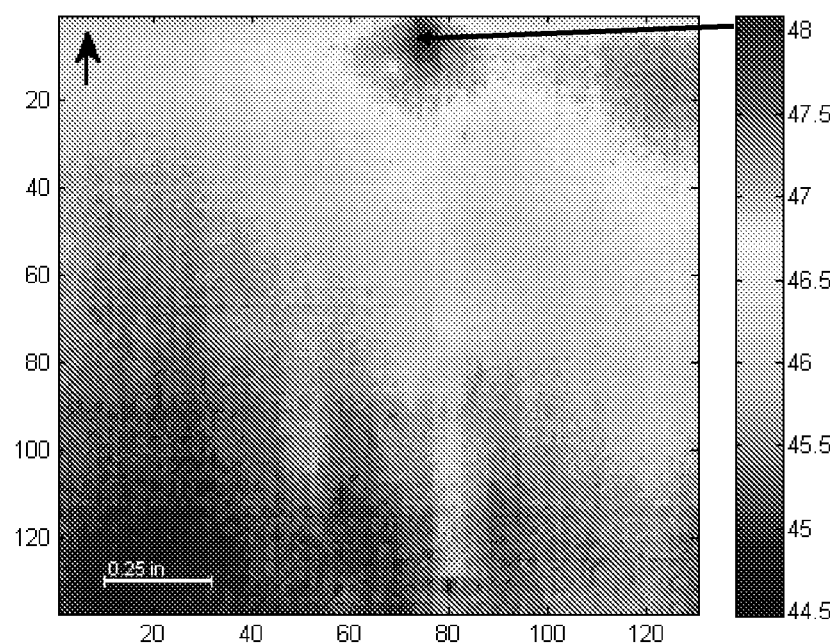
FIG. 8 shows a corrected microbolometer thermograph (streak/smudges) of the sample shown in FIG. 5 processed according to another embodiment of the present invention.
Figure 9:
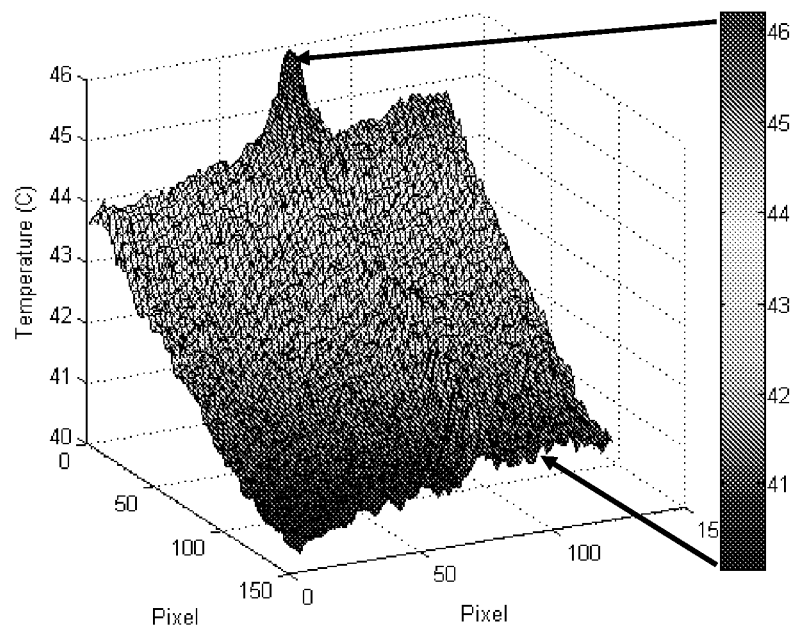
FIG. 9 shows a topological map (streak smudges) of the sample shown in FIG. 5 processed according to another embodiment of the present invention.

In FIG. 8 the thermograph is shown after the signal is corrected using a first order filter, and the defects are seen. Unless specified, all further thermographs have had the rolling read filter correction applied. A three-dimensional plot of the thermograph is shown in FIG. 9, which is another perspective that shows the topology of the film, including both the ridge and two smudges.

Figure 10:
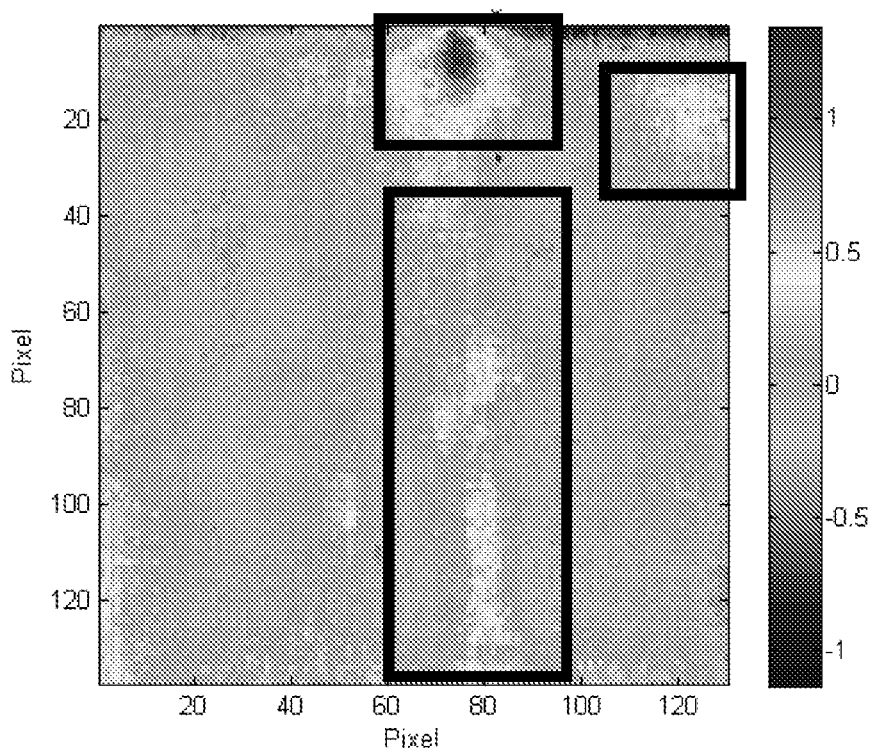
FIG. 10 shows a thermograph after best-fit plane subtraction (streak smudges) of the sample shown in FIG. 5 processed according to another embodiment of the present invention.

An acceptable film should have uniform thickness and uniform composition, and one-dimensional diffusion through it should result in a uniform planar thermograph. Thickness gradients will cause the plane to tilt and introduce some gentle variation in the film. Temperature variations from the uniform or tilted plane can be removed by subtracting a plane of best fit from the image and can isolate other defect types like streaks and smudges, as seen in FIG. 10. These manufacturing defects are deviations from the plane in excess of 0.5° C.

Figure 11:
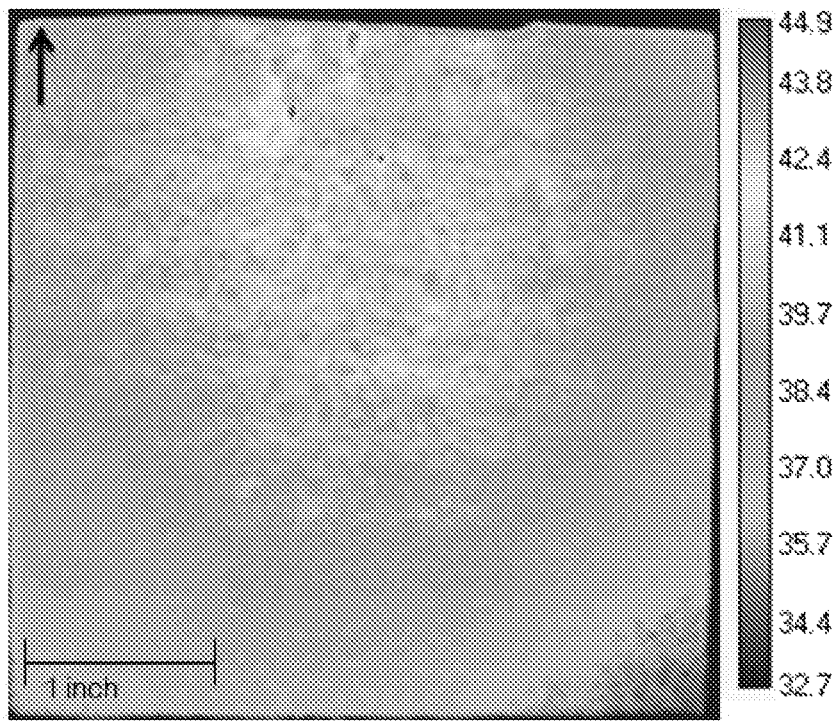
FIG. 11 shows a thermograph of film that is acceptably coated according to one embodiment of the present invention.
Figure 12:
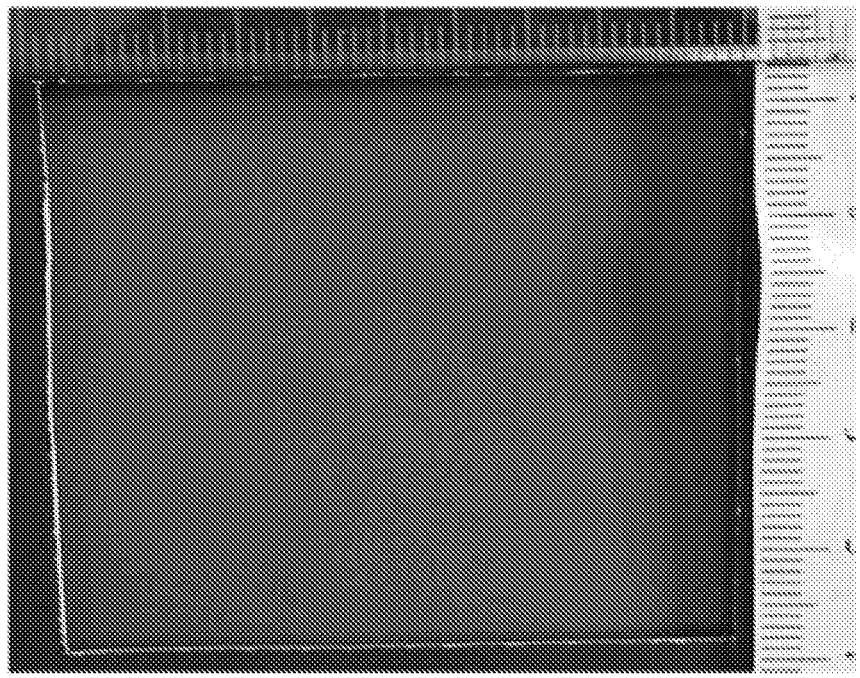
FIG. 12 shows a small thickness gradient sample (photo).

FIG. 11 is a thermograph from a good film obtained with the photon detector-based thermal camera. Temperature variations are minimal, under 1° C. Dark blue regions are cooler regions due to extra cooling at the edges of the sheet. Examination of the center region of the sheet reveals a set of small wavelike undulations perpendicular to the coating direction. These undulations can be seen when using the photon detector-based camera. However, these undulations are real and observed on a variety of films (both those produced in this laboratory as well as on commercial anode/cathode films). These undulations may be the result of the coating process—either a fluid mechanical instability or the interaction of the fluid with the elastomechanics of the coater assembly. This is the first time this type of manufacturing defect has been reported for anode/cathode battery coatings.

In FIGS. 12 through 15 the optical and thermal images of a smooth film are presented, where a thickness gradient running from top to bottom has been purposely imposed during manufacture of the film. Images were obtained using both camera types. In both FIG. 13 and FIG. 14, the top portion has reached a higher temperature sooner than the lower section, indicating faster thermal diffusion due to a thinner coating.

The imposed coating thickness gradient is a plane, since the coating blade is straight although the distance from the film was different on the two edges of the coater. Since this is a smooth film, the surface aberrations are small and thus exhibit a random pattern. The largest defects are +0.3° C., which was near the accuracy limit of the camera's calibration curve, with a slight 0.5° C. plateau region at the top.

Figure 15A:
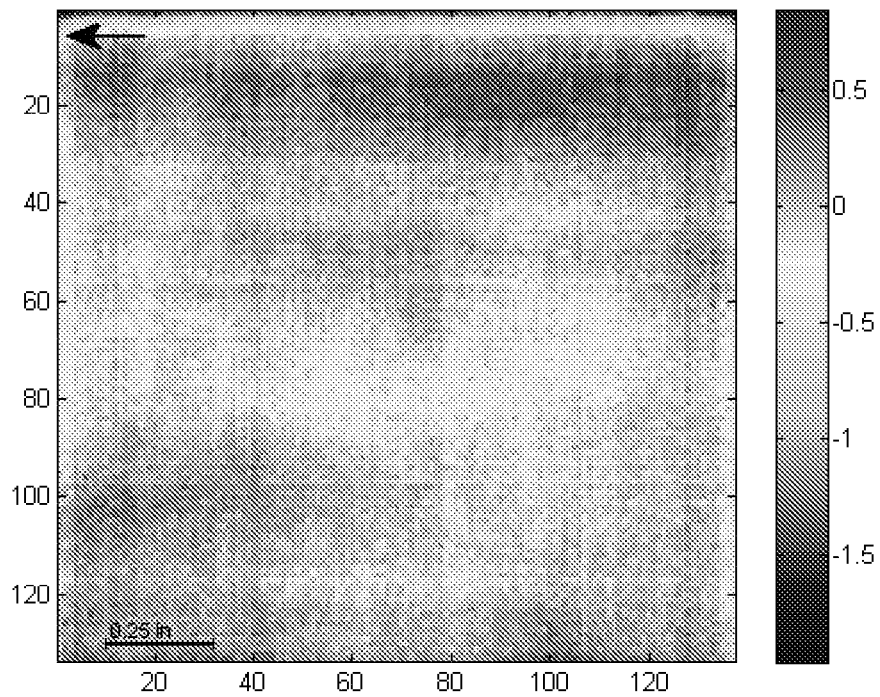
FIG. 15 shows a plane subtraction from a smooth film (a) and with the region enhanced (b) of the sample shown in FIG. 12 according to another embodiment of the present invention.
Figure 15B:
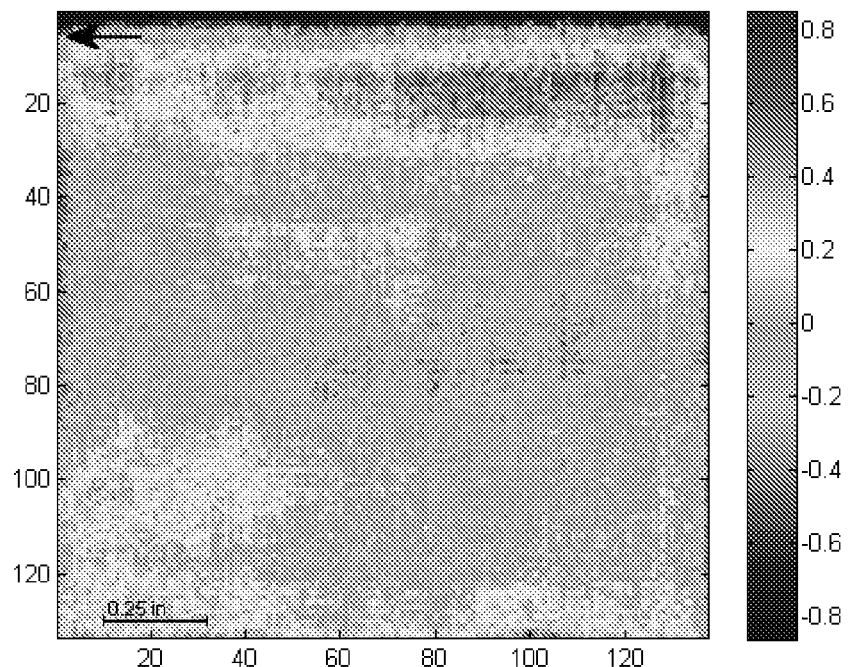

This response is different than the damaged film shown in FIGS. 17-28, where the features of the defect are 2° C.—nearly an order of magnitude greater. The thickness gradient is subtracted from the microbolometer image, and the results are shown in FIG. 15A, where now the remaining surface aberrations of the film are observed. If the small "hot region" in the upper right hand portion of the image in FIG. 15*a* is removed (i.e. an edge effect), then the enhanced thermal image is shown in FIG. 15*b* where the thermal differences of less than +0.2° C. on average are observed.

Figure 16:
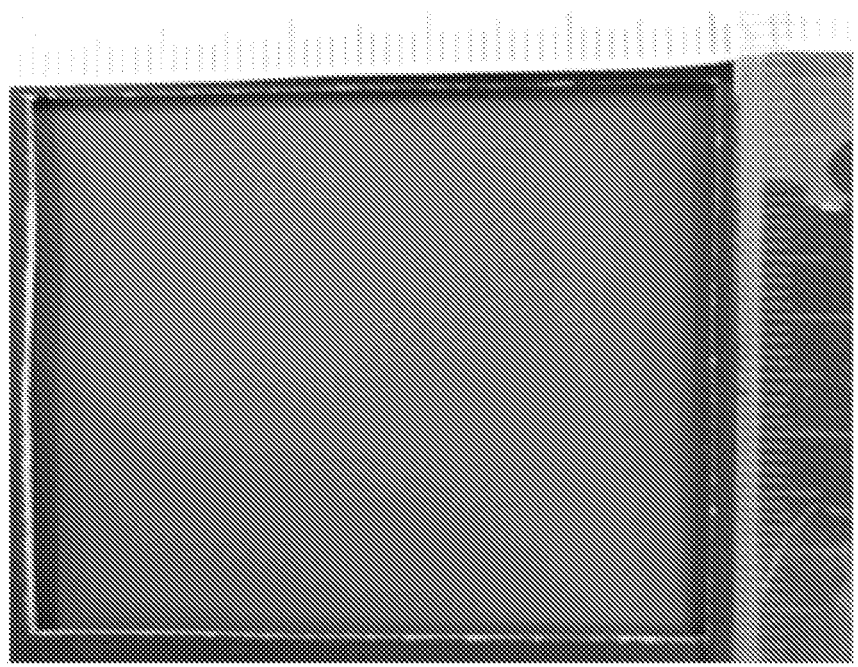
FIG. 16 is a photo of a ridged film sample
Figure 17:
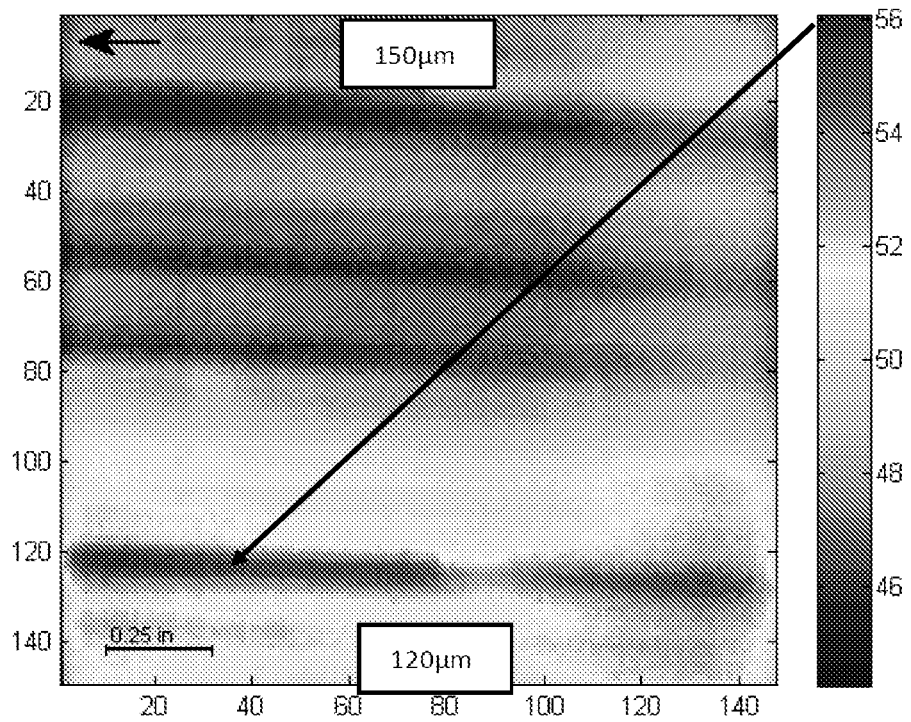
FIG. 17 is a thermograph of a ridged film of the sample of FIG. 16 according to another embodiment of the present invention.

Striations and thickness gradients that are difficult to observe optically can be identified using thermal imaging. FIGS. 16 and 17 are respectively a photograph and thermograph of a carbon-based anode film, where a wet coating thickness gradient of 150 μm to 120 μm was purposely applied during manufacture of the film (the top of the image is 150 μm that decreased linearly to 120 μm at the bottom).

Figure 18:
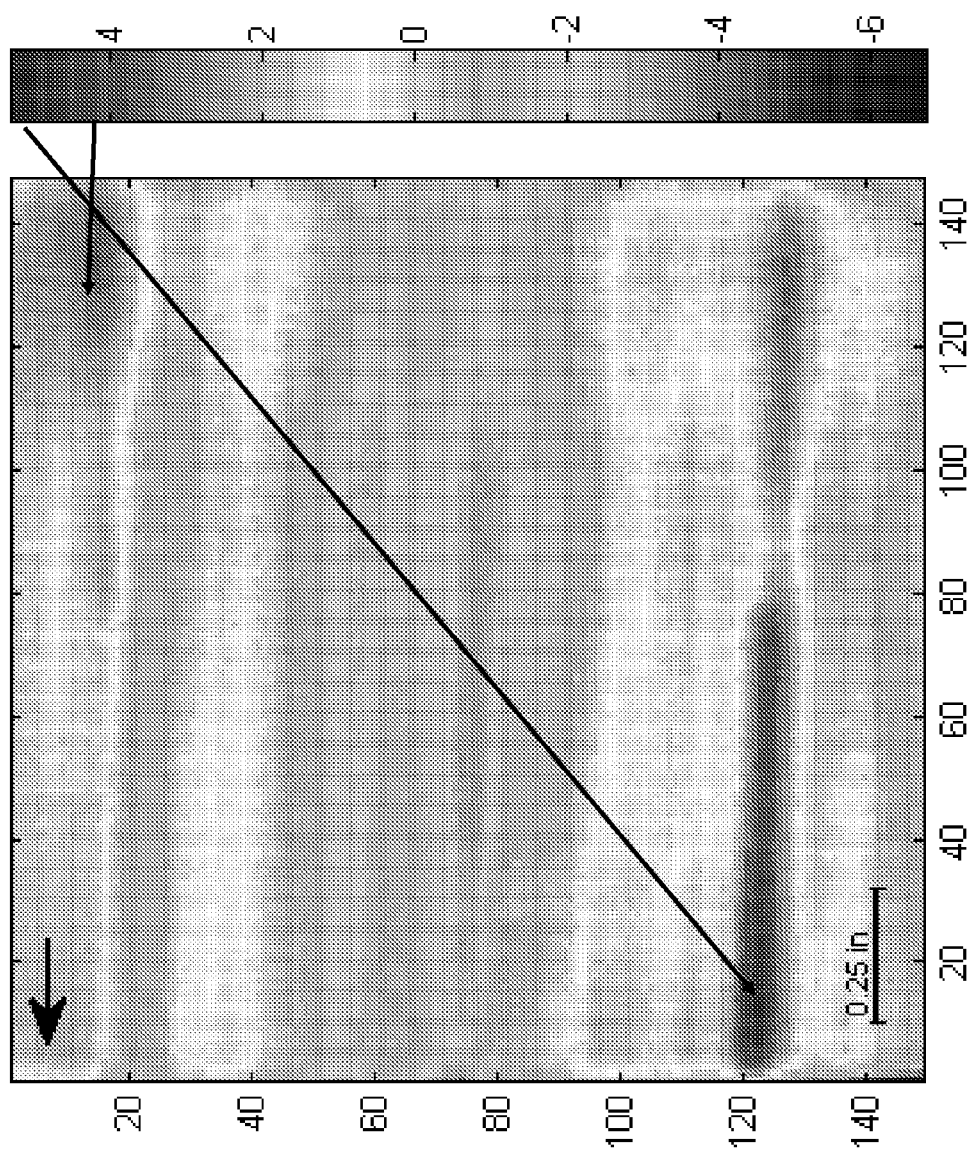
FIG. 18 shows a deviation from plane of the sample of FIG. 16 according to another embodiment of the present invention.

During evaporation of the solvent, the film thickness shrinks and ridges in the foil backing if it is not kept under sufficient tension while drying—a manufacturing defect. One defect is indicated by the box, although it is difficult to see in the photograph in FIG. 16. However, these manufacturing defects are evident in the nearly +3° C. temperature variations. The effect of the thickness gradient can be removed from the image, as shown in FIG. 18, where (i) a plane was determined via a least squares fit to the image in FIG. 17 and (ii) this plane was subtracted from the image in FIG. 17. This post-processing of the raw thermographs enhances observation of striation and other coating defects.

Figure 19:
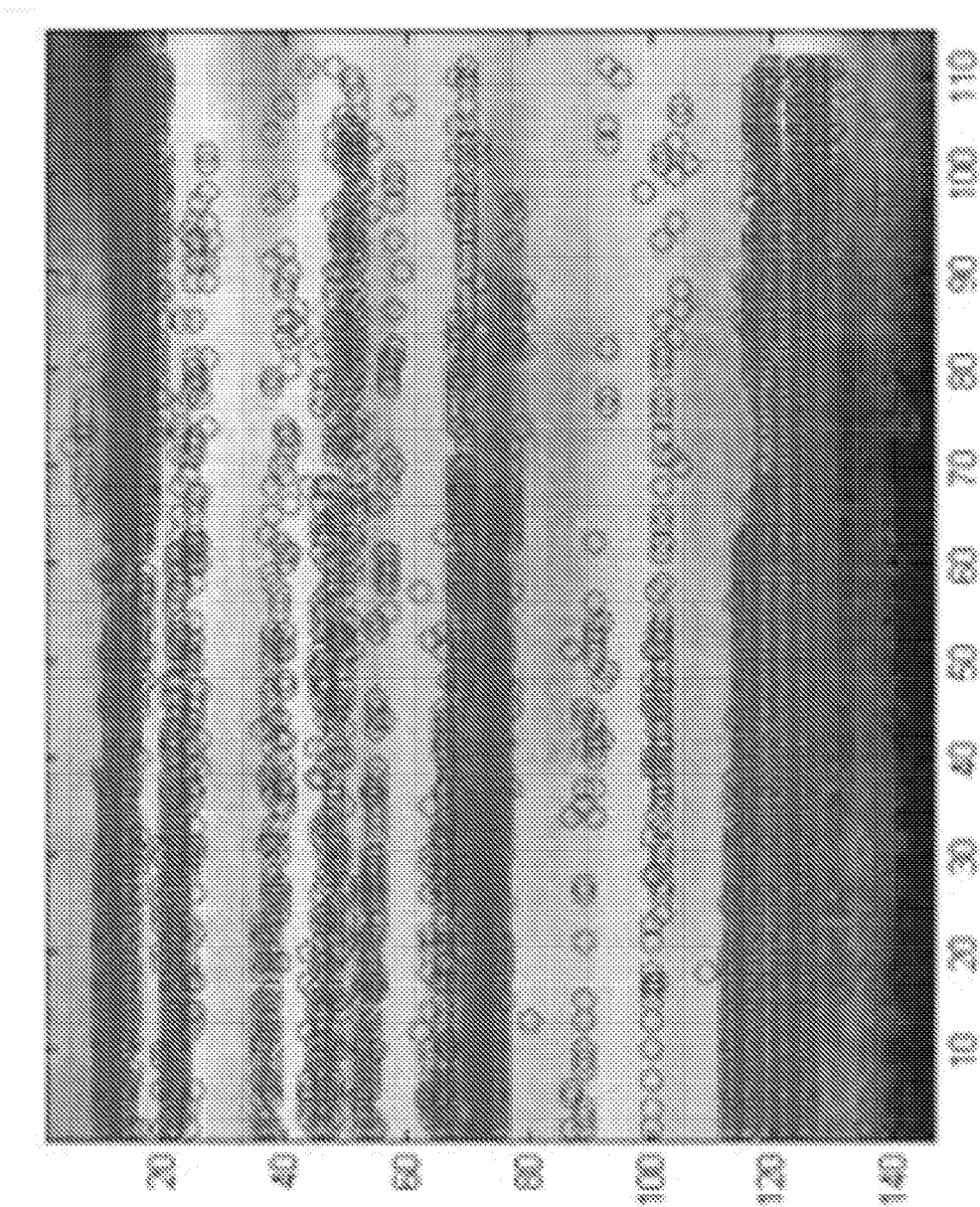
FIG. 19 shows an application of damage detection algorithm of the sample of FIG. 16 according to another embodiment of the present invention.

Image processing algorithms, such as the one described in FIG. 3, can be used on these corrected images to locate aberrations automatically. FIG. 19 shows the application of an edge detection algorithm for the image shown in FIG. 17, where the striations are identified by the algorithm and are shown graphically in red and green circles.

Figure 20:
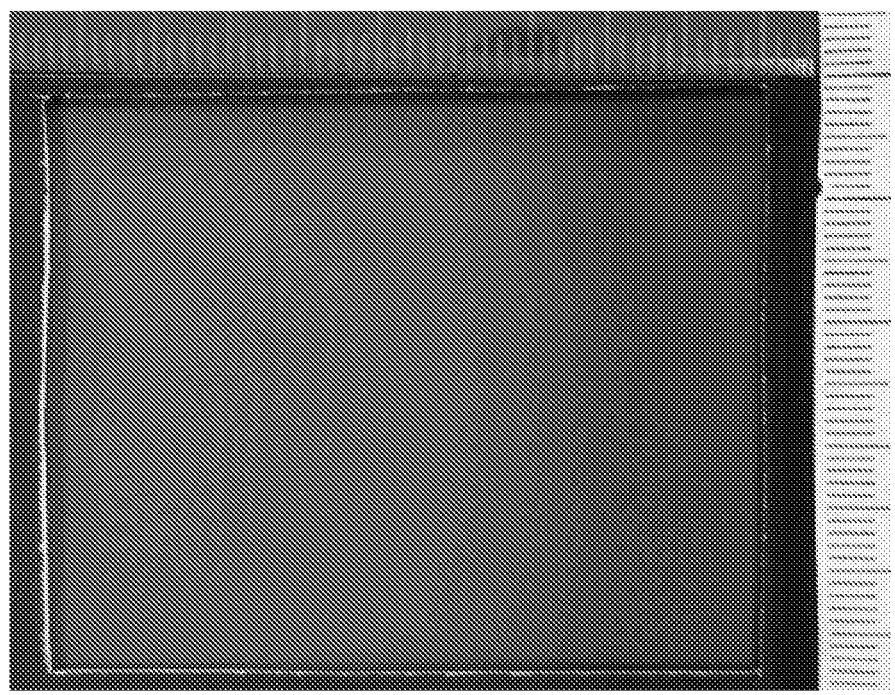
FIG. 20 is a photo of a ridged film sample.
Figure 21:
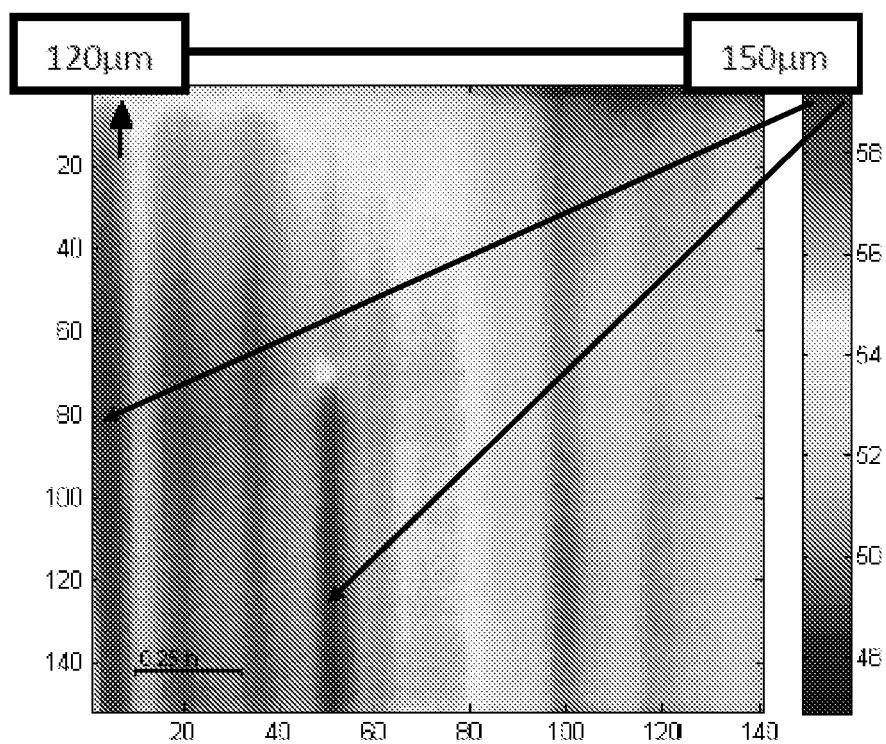
FIG. 21 is a thermograph of a ridged film of the sample of FIG. 20 according to another embodiment of the present invention.
Figure 22:
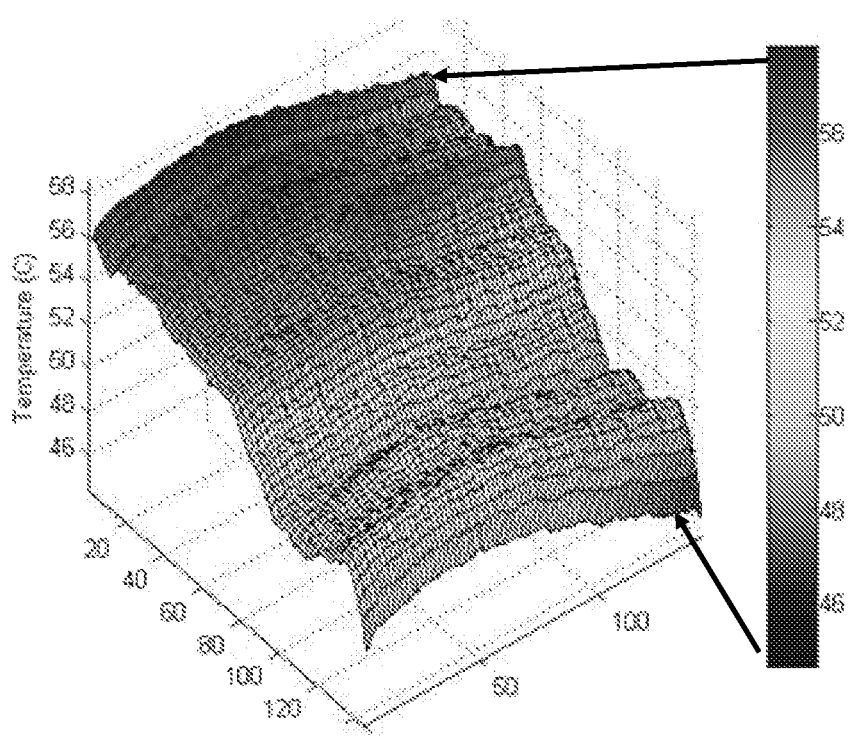
FIG. 22 shows a topological map of the sample of FIG. 20 according to another embodiment of the present invention.
Figure 23:
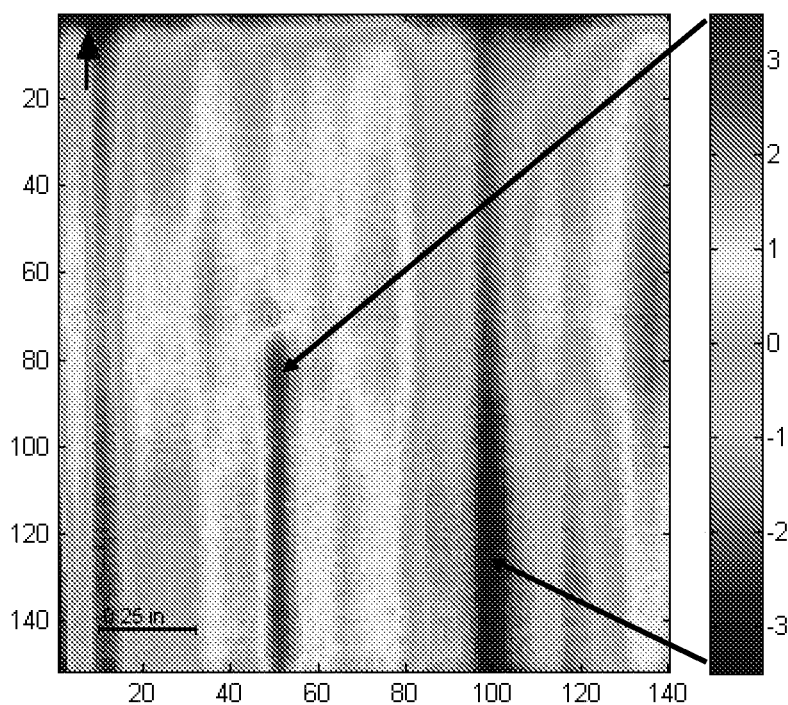
FIG. 23 shows a deviation from plane of the sample of FIG. 20 according to another embodiment of the present invention.

The left to right thickness gradient introduced to the film of FIG. 20 is viewed in the corresponding thermograph of FIG. 21. The thickness gradient is indicated on the topographical map by a sharply angled plane, seen in FIG. 22. Striations introduced in the drying process and their deviations relative to this gradient remain visible, especially once the thickness gradient is subtracted in FIG. 23. Again, defects cause temperature variations that are four to five times greater than the image noise.

Also of interest on this film is a small droplet, roughly 1 mm in diameter which appeared during the film coating process. Small gas pockets or solid droplets that form during film production create features in the thermal image. These defects are seen on the thermographic image, but are difficult to discern using traditional photographic images, (even when the image is enhanced by taking the photograph at an angle), as seen in the comparison shown in FIG. 24. The thickness gradient indicated in FIG. 24a was the thickness of the wet film as applied during the coating step. After drying, the film thickness decreases as the solvent evaporates.

Figure 25:
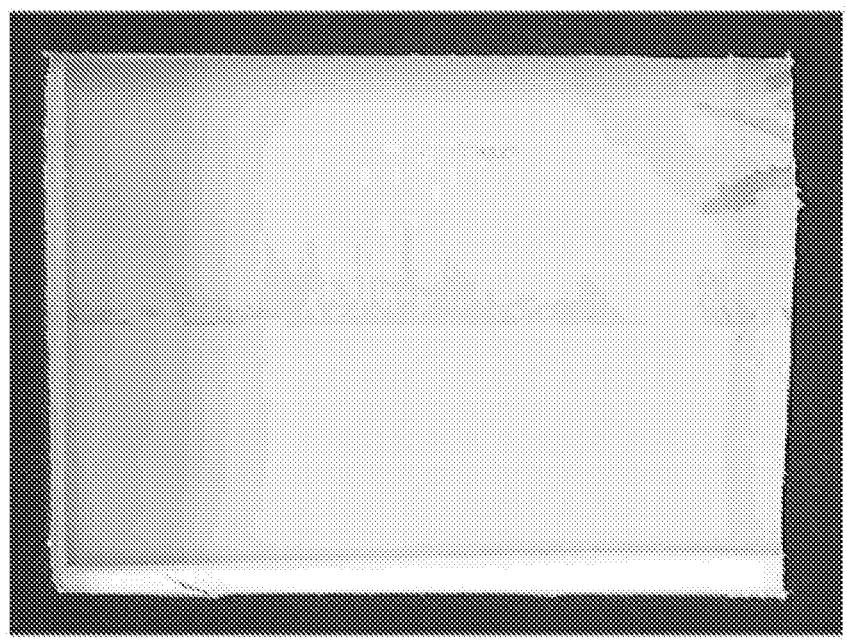
FIG. 25 is a photo of a contaminated current collector sample.
Figure 26:
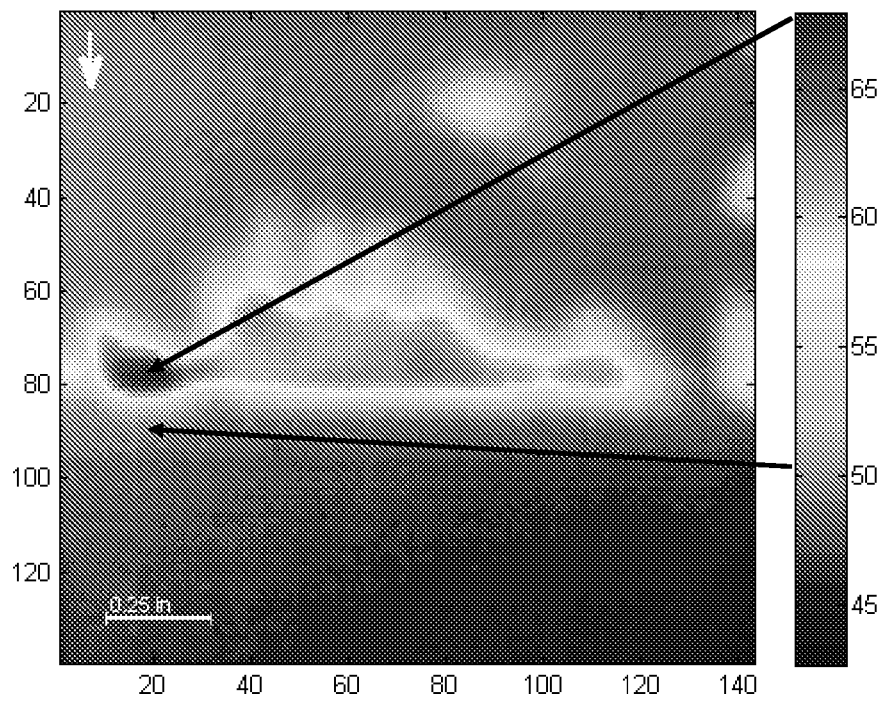
FIG. 26 is a thermograph of a contaminated current collector of the sample of FIG. 25 according to another embodiment of the present invention.
Figure 27:
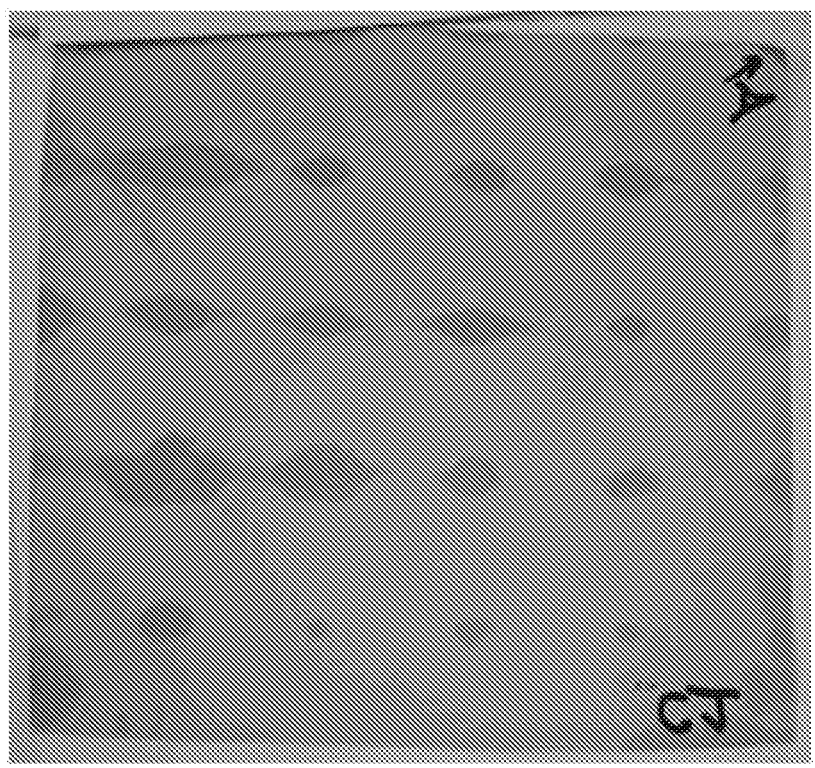
FIG. 27 is a photo of an oil contamination (foil side) sample.
Figure 28:
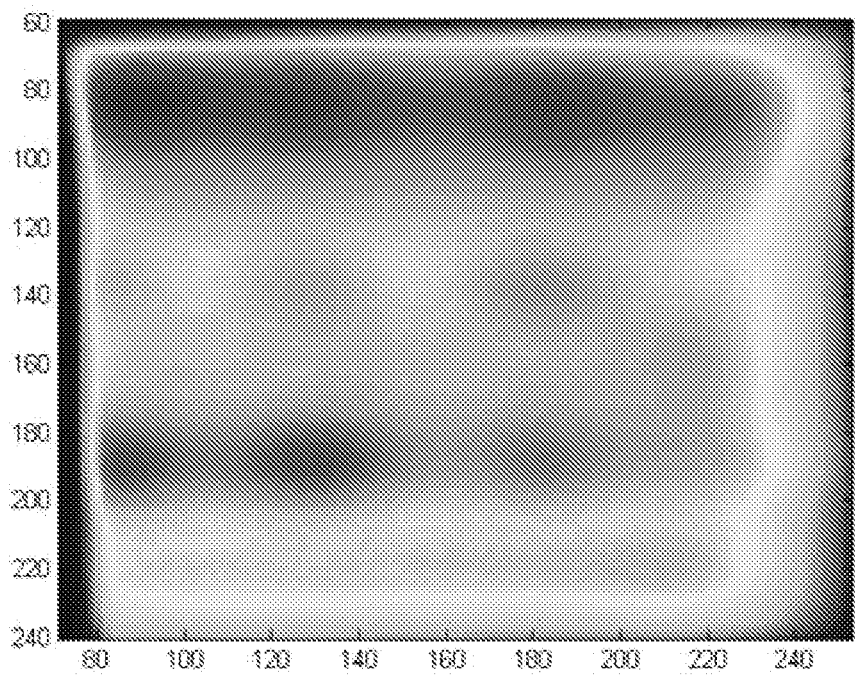
FIG. 28 is a thermograph of an oil contamination (film side) of the sample of FIG. 27 according to another embodiment of the present invention.

FIGS. 25 and 26 show the result of current collector contamination by the coating material. Though optically visible, this contaminant is on the underside of the coated film and is thus difficult to observe. This film also has a left to right thickness gradient, but the coating contaminant on the metal side dominates the thermal image, because this contaminant greatly increases absorption of the radiative pulse on the typically reflective metal surface. This particular type of flaw is readily identified by a large temperature difference of 35° C. in the thermograph as compared to the typical thermal aberrations that are much smaller.

An oil stain on the metallic film is shown in FIGS. 27 and 28, where again the thermal image has large aberrations. Since oil is present as a lubricant in most industrial processes, but undesirable inside of batteries, early contamination detection is valuable.

Figure 29:
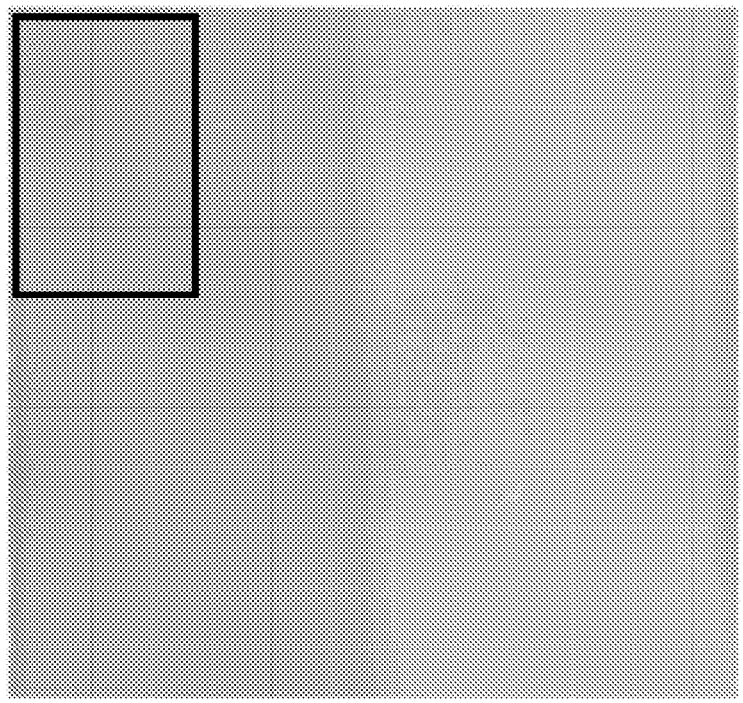
FIG. 29 is a photo of a large composition difference sample.
Figure 31:
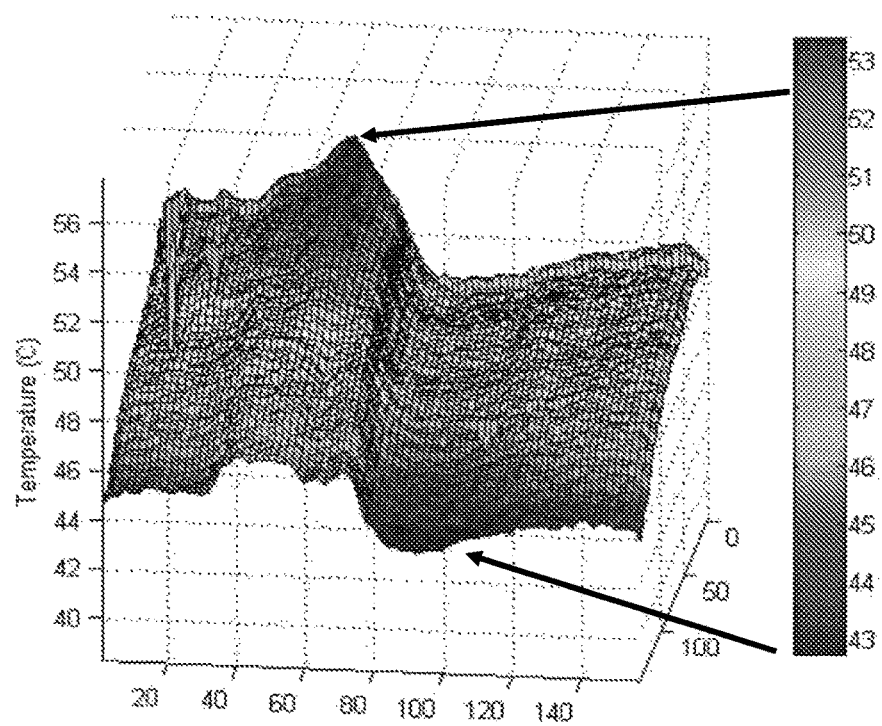
FIG. 31 shows a topological map (large composition difference) of the sample of FIG. 29 according to another embodiment of the present invention.

Pulse thermography can also detect composition differences. A composition difference (e.g. the relative concentration of active material vs. carbon black) causes the thermal conductivity of the material to change, which affects the diffusion time in a similar manner as a thickness gradient. FIGS. 29 and 30 are of an anode film where the composition of active material differs by 16% between the left and right side. The thermograph distinguishes the two regions and identifies small droplets in the upper left corner, which an observer may not note from the photograph. The left side has a composition (by weight) of 64% graphite, 18% PVDF, and 18% carbon black. The right side has a composition of 80% graphite, 10% PVDF, and 10% carbon black. The 3D plot shown in FIG. 31 shows the change in thermal intensity, and hence composition, as detected via flash thermography.

Figure 32:
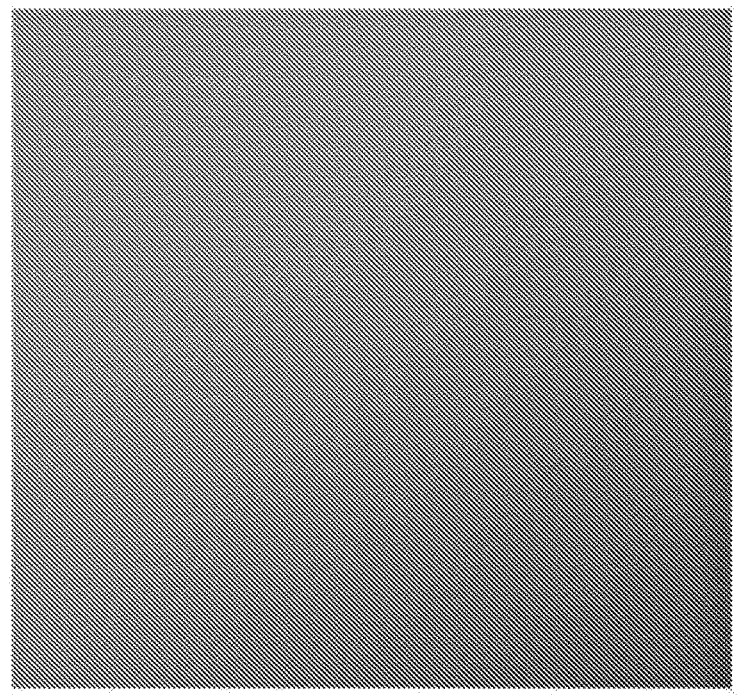
FIG. 32 is a photo of a small composition difference sample.
Figure 33:
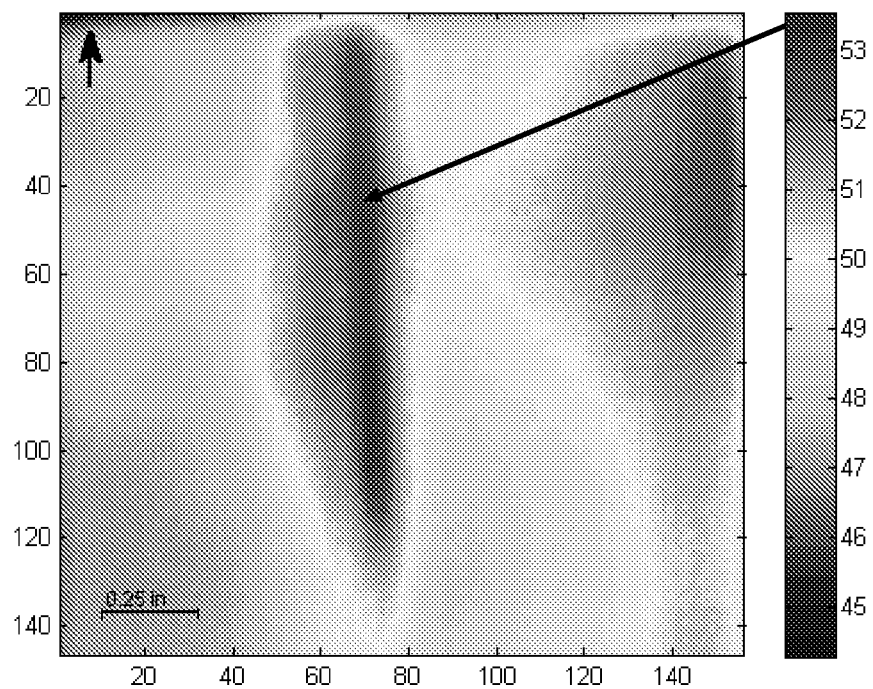
FIG. 33 is a thermograph of a small composition difference of the sample of FIG. 32 according to another embodiment of the present invention.

These large composition differences can be detected optically as shown in the gray shade differences in FIG. 29. However, flash thermography can detect smaller composition differences that cannot be optically detected. FIG. 33 demonstrates how smaller composition changes of −2% are detected using flash thermography, although the composition difference is optically undetectable as shown in FIG. 32. The composition of the left side is (by weight) 80.0% graphite, 10.0% carbon black and 10.0% PVDF. The right side is 78.4% graphite, 10.8% carbon black, and 10.8% PVDF. The center displays a streak that resulted from the interface at the overlap of coatings.

Figure 34:
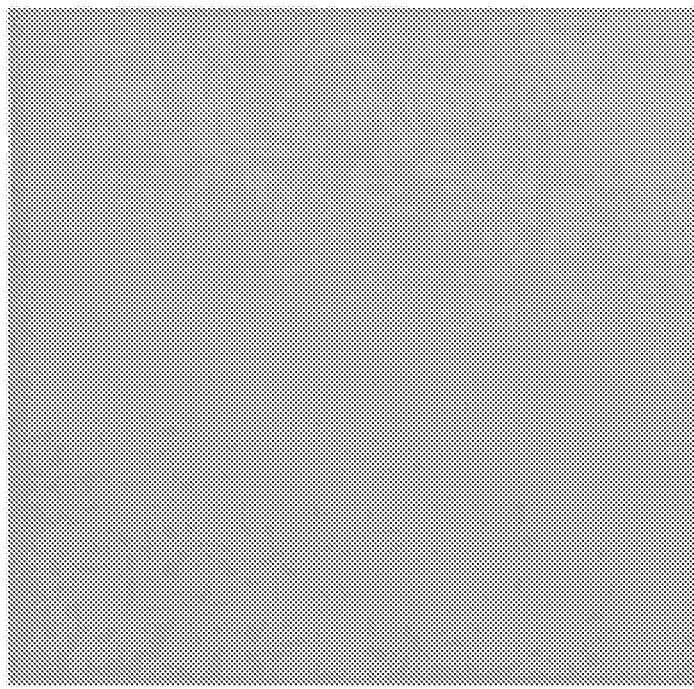
FIG. 34 is a photo of a mottled film sample.
Figure 35:
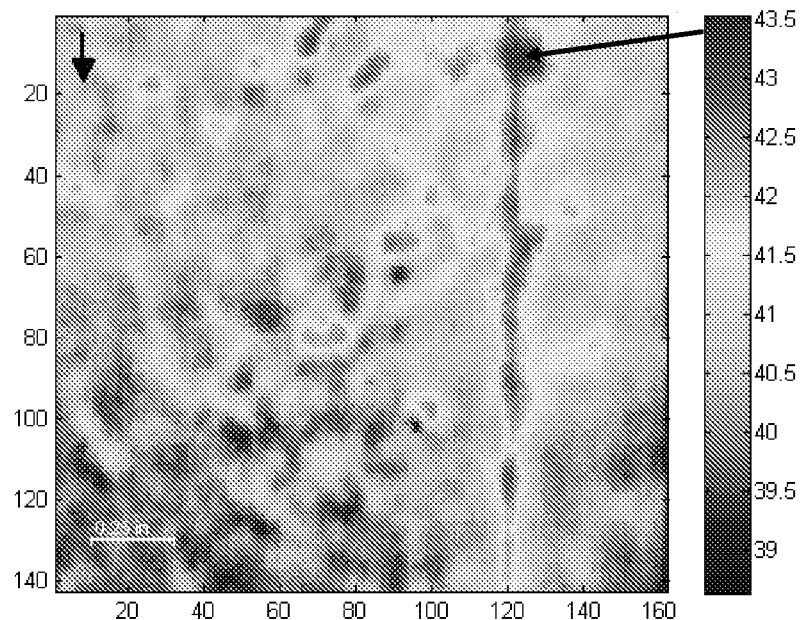
FIG. 35 is a thermograph of a mottled film of the sample of FIG. 34 according to another embodiment of the present invention.
Figure 36:
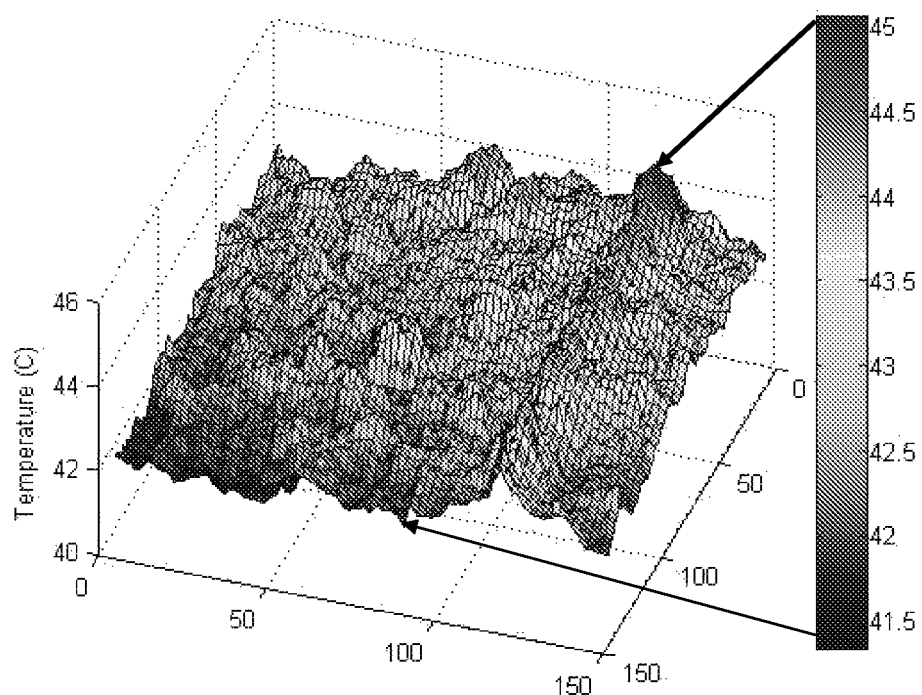
FIG. 36 shows a topological map of the sample of FIG. 34 according to another embodiment of the present invention.
Figure 37:
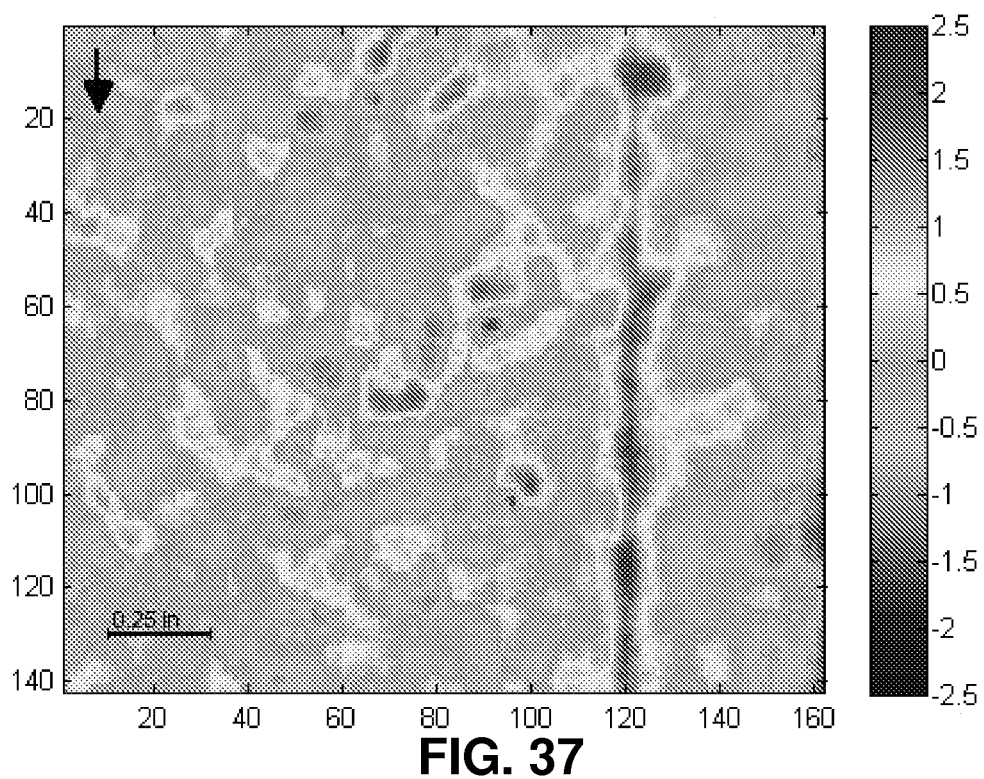
FIG. 37 shows a plane subtraction of the sample of FIG. 34 according to another embodiment of the present invention.

Poor mixing of the components in the anode or cathode can degrade battery performance. In FIG. 34 shows is a photo of a film that appears to be free of any thickness distortions; however, the coating was poorly mixed, by design, prior to applying the coating. The thermograph in FIG. 35 shows mottling and spots that indicate the poor mixing of the precursor materials. A topological map and use of the plane subtraction algorithm are useful for identifying these spots, as viewed in FIGS. 36 and 37. The ridge stands out with a 3° C. magnitude, but the mixing imperfections are detected with deviations above the average plane of approximately 1° C. Thus, the flash thermography method can detect poorly mixed battery coating materials.

Figure 38:
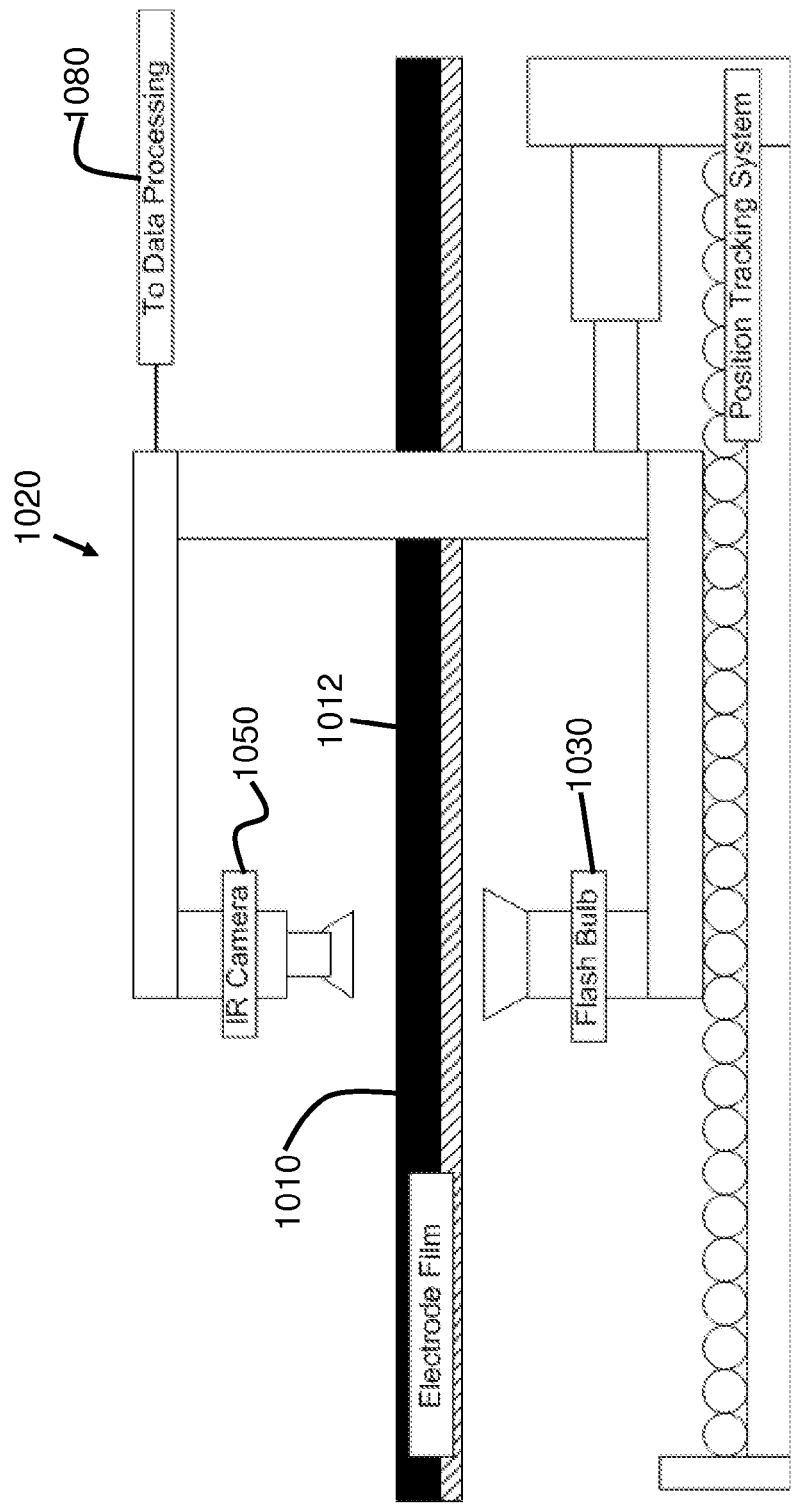
FIG. 38 is a schematic representation of a system for analyzing a coating process according to another embodiment of the present invention.

One embodiment of the present invention pertains to a method of on-line quality control for a battery manufacturing assembly line. Because the flash thermography is fast, it is possible for the technique to keep pace with industrial production. Two possible modes of use are:

1. During robotic assembly of the anode and cathode sheets with the separator into the cells, the individual electrode sheets pass through a flash thermography unit prior to assembly into the battery cell. The highest quality cells can be sorted and sold at a premium for the most demanding applications, less than perfect cells can be sorted for lower intensity operations (at less than premium prices) and bad cells can be robotically rejected.
2. The unit is installed on the production line after the sheets have been dried and either before and/or after the compaction step. This continuous flash thermography set-up is shown schematically in FIG. 38. The flash bulb and IR camera are mounted in an assembly which travels along at the same speed as the film line. Once this section of the film has been scanned, the assembly resets to its start position and begins scanning the next portion of the film line. Defective regions are ejected once they are cut out.

In either of these two potential modes of operation, this process information can be used as direct feedback to the manufacturing process to improve the yield of the highest quality cells. It is understood that these two possible modes of usage are presented by examples only, and are not meant to be limiting.

A third mode of use is with the flash bulb fixed at one point and the IR camera fixed at a point downstream. It is understood that the aforementioned three modes of use are by way of example only, and are not to be construed as limiting. Yet other embodiments of the present invention contemplate additional variations in the placement of the recording sensor and the radiation source.

Figure 39:
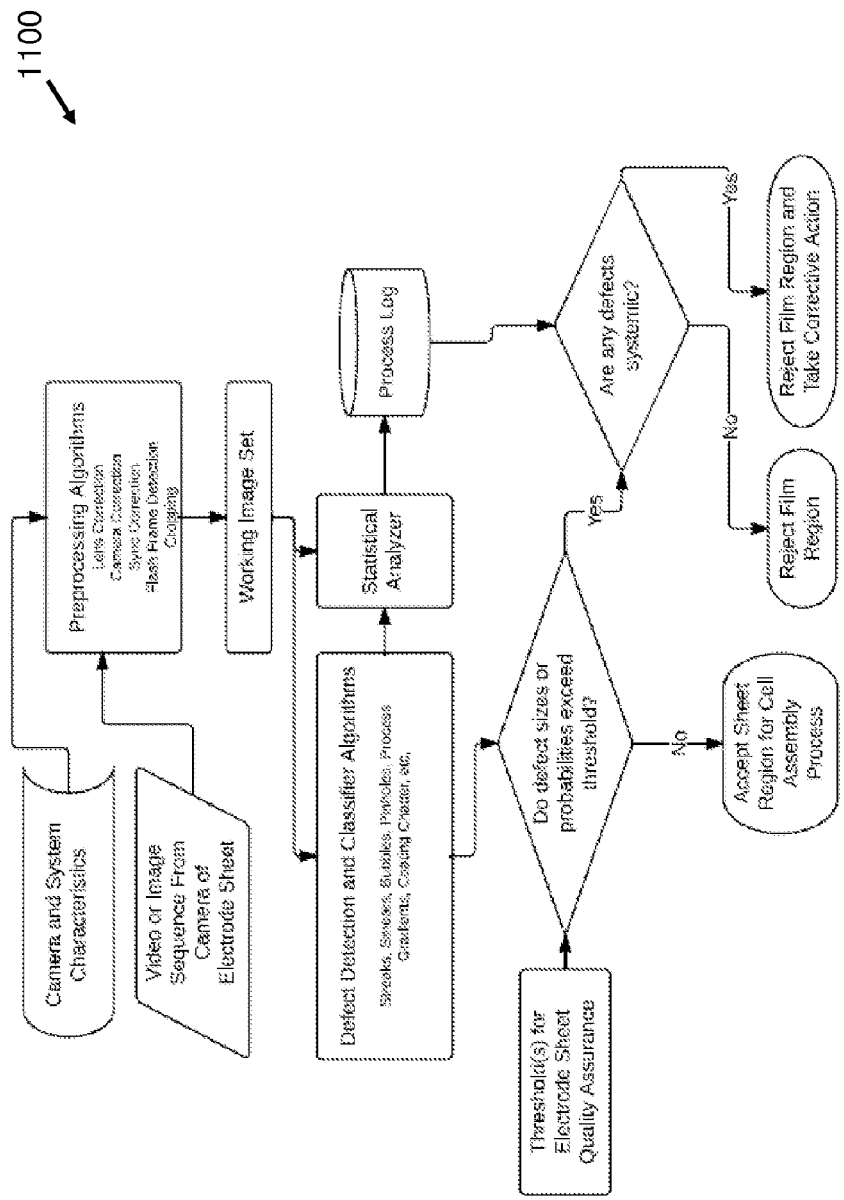
FIG. 39 is a flow chart of an image processing algorithm according to one embodiment of the present invention.

Various embodiments of the present invention pertain to a signal processing algorithm 1100 shown schematically in FIG. 39. In some embodiments this algorithm is used to in analyze cut electrode sheets or those on a flat film line.

In one form, the algorithm assumes 1100 that the film is locally flat with dominate thermal diffusion in the through-plane direction for the timescale of interest. A film of uniform thickness and composition will exhibit the same response over many points at any given time, where deviations from this response indicate flaws in the film casting process or substrate contamination. Some of the local film thickness and composition variance is contained in the first few frames after the flash breakthrough. A single image can be used to identify most defects.

The video or sequence of images recorded by the camera is transferred to a computer which applies a predetermined set of preprocessing algorithms. These algorithms remove artifacts introduced by the camera hardware, such as lens distortion, dead pixel regions, microbolometer rolling read smear, and, if using multiple camera arrays, can stitch together the images and compensate for synchronization offsets. They also identify the image(s) immediately following flash breakthrough and crop the background edges from the sequence. This adjusted image or set of images, termed the working image set, is transferred to the next section of the algorithm.

The working image set is processed by a sequence of defect detection and classifier algorithms. Each algorithm looks for a specific defect type using image signal processing techniques and attempts to quantify the extent of that defect's presence. For example, the algorithm for pinhole detection (where a coating fails to adhere to the substrate at small points) looks for single pixel points which are much greater in their intensity than the neighborhood pixel mean. Defects such as streaks and smears, bubbles, process gradients, and coating chatter, are identified using similar, but more complex methods. The results from the algorithms are passed to a decision engine and to a statistical analyzer module.

The statistical analyzer module aggregates detected defects and their incidence along with process trends, such as an increasing film baseline response due to heating of the film line over time. This process information is logged for quality assessment and system diagnostics. It can also be analyzed to look for evidence of a gradual process departure from normal conditions that the specific-defect detection algorithms do not detect.

The decision engine examines the number and scale of detected defects and compares them with defined threshold limits. If a sheet or sheet region fails inspection, it is rejected and excluded from assembly into a battery. If defects are present, a trending identification module looks at the process log to determine if the defects are isolated or if corrective maintenance is required.

This algorithm allows for specific defects to be identified automatically if their characteristics can be well-defined or classified. Its capabilities can be expanded simply by adding more defect detection classifications to the defect detection phase. It also does not rely on a thermal model for baseline computations, meaning material properties are not required for analysis.

The paragraphs that follow express various embodiments of the present invention:

X1. One embodiment pertains to a method for monitoring a manufacturing process. The method preferably includes providing a thin film component having two sides, a source of energy, and a radiation sensor, pulsing energy from the source onto the thin film component, and detecting radiation with the sensor from the thin film component.

X2. Another embodiment pertains to a system for monitoring a process for manufacturing a thin film component. The system preferably includes a sensor providing a signal corresponding to the temperature of the film of the thin film component, an actuatable source of radiation adapted and configured to emit radiation in short pulses directed at the thin film component, and a computer, said computer being operably connected to said source to actuate a pulse, said computer preparing data corresponding to the signal.

Yet other embodiments pertain to any of the previous statements X1 or X2, which are combined with one or more of any of the following other aspects, it being understood that such combinations can be considered logically without need for an antecedent basis:

Which further comprises repeating said pulsing, said detecting, and said preparing in a substantially continuous manufacturing processor a batch manufacturing process.

Wherein said pulsing is for a first time period and said detecting is for a second time period that occurs after the first time period.

Wherein said detecting is a first detecting, and which further comprises a second detecting of radiation, said second detecting occurring after said first detecting, wherein both said first detecting and said second detecting occur after the same single pulse of energy.

Wherein said pulsing is a single pulse, and which further comprises preparing a thermal image of said component after said detecting, and.

Which further comprises correcting the thermal image with a time-based first order filter, or correcting the thermal image by calculating a plane of best fit of the image, or correcting the thermal image by adjusting the image with a planar representation of the image, or correcting the thermal image by detecting edges, or comparing the thermal image to a baseline image.

Wherein said providing includes a computer receiving information from the sensor, and which further comprises assigning a quality status to the component by the computer.

Which further comprises capturing a thermal image of the component before said pulsing.

Wherein the thermal image is a first thermal image, and which further comprises capturing a second thermal image of the component after said detecting and correcting the second thermal image with the first thermal image.

Wherein the source of energy substantially emits in a first spectrum and the sensor substantially detects in a second spectrum different than the first spectrum, or the source of energy emits energy with a first peak wavelength and the sensor substantially detects energy at a second peak wavelength different than the first peak wavelength.

Wherein said sensor includes a photon detector, or the sensor is a bolometer, or the sensor is a microbolometer, or said sensor detects infra-red radiation, or said sensor detects millimeter wave radiation, or said pulsing is for less than about one tenth of a second.

Which further comprises shielding the sensor from direct receipt of the pulsing energy.

Wherein the component is generally isothermal before said pulsing, or thermally conditioning the component by heating or cooling before measuring the thermal gradient.

Wherein said detecting is before compacting of the coating, or said detecting is after compacting of the coating, or said detecting is after drying of the coating.

Wherein the component has a thickness, a length, and a width, and the thickness is substantially less than either the width or the length.

Wherein the component includes substantially planar metallic foil having a coating on the other side, or the component is one of a cathode or anode, or the component is used in a lithium-ion battery, or the component is used in either of a silver-zinc battery or a nickel metal hydride battery.

Which further comprises capturing a thermal image of the component after a single pulse of energy.

Which further comprises delaying said capturing until after the single pulse is substantially complete.

Wherein said capturing is a first thermal image, and which further comprises capturing a second thermal image after the first thermal image.

Wherein said capturing a second thermal image is before the substantially one dimensional thermal response through the thickness of the thin film battery component dissipates in lateral directions.

Which further comprises capturing a thermal image of the component before the substantially one dimensional thermal response through the thickness of the thin film battery component dissipates in the thickness and width of the thin film battery component.

Wherein the thermal image is a first thermal image, and which further comprises capturing a second thermal image of the component after said detecting, and correcting the second thermal image with the first thermal image.

Wherein the thin film battery component is substantially continuous, or the thin film battery component is sized to fit within a battery.

Wherein said sensor has an inlet for receiving radiation, said source is oriented to emit radiation generally toward the inlet, and said sensor and said source are located such that the battery component substantially blocks radiation from being received through the inlet.

Wherein said software creates data corresponding to the signal from a single pulse of said source.

Wherein the data corresponds to a two dimensional representation of the temperature of the battery component, or the data includes a two dimensional representation of the thickness of a coating of the battery component, or. the data includes a two dimensional representation of the uniformity of a coating of the battery component, or the data includes a representation of nonadhered coating on the battery component, or said software uses the signal to detect defects in the battery component.

Wherein the thin film battery component has been severed from a larger section of thin film material, and said software uses the signal to detect debris on the component from the severing operation.

Wherein said software uses the signal to detect particles on the surface of film of the thin film battery component.

Wherein said software activates a short pulse of radiation, and said software records the signal after the pulse has ended.

Wherein the thin film battery component has a thermal time constant TAU wherein:

$$TAU \approx (THICKNESS**2)/ALPHA$$

wherein THICKNESS is the thickness of the component; ALPHA is the thermal conductivity of the component; and $\approx$ means corresponds approximately equal to;

said source is adapted and configured for producing an energy pulse having a width, and the width is less than the quantity [about 2×TAU], or the width is less than about one half of TAU.

Wherein the thin film battery component has a thermal time constant TAU wherein:

$$TAU \approx (THICKNESS**2)/ALPHA$$

wherein THICKNESS is the thickness of the component; ALPHA is the thermal conductivity of the component; and $\approx$ means corresponds approximately equal to;

said source is adapted and configured for producing an energy pulse having a beginning and an ending, said detecting begins at a time T, and the interval from the end of the pulse to time T is less than the quantity [about 4×TAU], or the interval from the end of the pulse to time T is less than TAU.

Wherein the thin film battery component has a thermal time constant TAU wherein:

$$TAU \approx (THICKNESS**2)/ALPHA$$

wherein THICKNESS is the thickness of the component; ALPHA is the thermal conductivity of the component; and $\approx$ means corresponds approximately equal to;

wherein the interval from said first detecting to said second detecting is greater than TAU.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method for monitoring a process for manufacturing batteries, comprising:
   providing a thin film battery component having two opposing sides, a source of energy, and a radiation imaging sensor;
   moving the thin film battery component in a direction;
   pulsing energy from the source onto one side of the thin film battery component;
   detecting radiation with the sensor from the other side of the thin film battery component;
   moving the sensor in the same direction during said detecting;
   capturing at least one thermal image with the sensor of the other side after said pulsing and before the substantially one dimensional thermal response through the thickness of the thin film battery component dissipates in the thin film battery component; and
   identifying a defective region of the thin film battery component from the at least one thermal image.

2. The method of claim 1 wherein said pulsing is for a first time period and said detecting is for a second time period that occurs after the first time period.

3. The method of claim 1 wherein said pulsing is a single pulse, and which further comprises preparing a thermal image of said component after said detecting.

4. The method of claim 3 which further comprises correcting the thermal image with a time-based first order filter.

5. The method of claim 3 which further comprises correcting the thermal image by calculating a plane of best fit of the image and modifying the image with the plane.

6. The method of claim 1 which further comprises capturing a thermal image of the component before said pulsing.

7. The method of claim 1 wherein the source of energy substantially emits in a first spectrum and the sensor substantially detects in a second spectrum different than the first spectrum.

8. The method of claim 1 wherein said pulsing is for less than about one tenth of a second.

9. The method of claim 1 wherein the component has a coating applied on the other side.

10. The method of claim 1 wherein the component includes substantially planar metallic foil having a coating on the other side.

11. The method of claim 1 wherein the thin film battery component has a thermal time constant TAU wherein:

$$TAU \approx (THICKNESS^2)/ALPHA$$

wherein THICKNESS is the thickness of the component; ALPHA is the thermal conductivity of the component; said source is adapted and configured for producing an energy pulse having a width, and the width is less than the quantity about 2×TAU.

12. The method of claim 1 wherein said identifying is with a temperature gradient on the image.

13. The method of claim 1 wherein said capturing is during a period in which the temperature of said other side is increasing.

14. The method of claim 1 wherein said capturing occurs before said other side experiences a peak temperature.

15. The method of claim 1 wherein the pulse of energy has a time duration that is less than about one TAU, wherein the thin film battery component has a THICKNESS and a thermal conductivity ALPHA; wherein $$TAU \approx (THICKNESS^2)/ALPHA.$$

16. The method of claim 1 wherein the pulse of energy has a time duration and said capturing occurs more than about one TAU after the end of the time duration, wherein the thin film battery component has a THICKNESS and a thermal conductivity ALPHA; wherein $$TAU \approx (THICKNESS^2)/ALPHA.$$

17. The method of claim 1 wherein said capturing is of a plurality of thermal images with the sensor of said other side after said pulsing and before the substantially one dimensional thermal response through the thickness of the thin film battery component dissipates in width of the thin film battery component, and said identifying is from the plurality of thermal images.

18. The method of claim 17 wherein said capturing is during a period in which the temperature of said other side is increasing.

19. The method of claim 18 above wherein said capturing occurs before said other side experiences a peak temperature.

20. The method of claim 19 above wherein said identifying is with the temperature gradients of several of the images.

21. A system for monitoring a process for manufacturing a thin film battery component, comprising:
an imaging radiation sensor providing a signal corresponding to the temperature of the film of the thin film battery component;
an actuatable source of radiation adapted and configured to emit radiation in repetitive short pulses directed at the thin film battery component; and
a computer having memory and software, said computer being operably connected to said source to actuate a series of pulses, said software preparing image data in memory corresponding to the signal;
wherein said sensor and said source are arranged on opposite sides of the thin film battery component;
wherein the signal is acquired within a time period beginning when a pulse is first emitted and ending before a time of about 4×TAU after the end of the pulse,
wherein:
the thin film battery component has a THICKNESS and a thermal conductivity ALPHA; and $$TAU \approx (THICKNESS^2)/ALPHA, \text{ and}$$

which further comprises a conveyor for moving the thin film battery component in a direction, and a position tracking system supporting said sensor, said position tracking system being movable in the direction.

22. The system of claim 21 wherein said sensor has an inlet for receiving radiation, said source is oriented to emit radiation generally toward the inlet, and said sensor and said source are located such that the battery component substantially blocks radiation from being received through the inlet.

23. The system of claim 21 wherein said sensor and the thin film battery component move in relative relationship to each other.

24. The system of claim 21 wherein the component is one of a cathode or anode.

25. The system of claim 21 wherein said software creates data corresponding to the signal from a single pulse of said source.

26. The system of claim 25 wherein the data corresponds to a two dimensional representation of the temperature of the battery component.

27. The system of claim 21 wherein said software activates a short pulse of radiation, and said software records the signal after the pulse has ended.

28. The system of claim 21 wherein the component thermally responds to the pulse, and said software prepares image data from a signal corresponding to the thermal response before the substantially one dimensional thermal response dissipates in the thin film battery component.

* * * * *